United States Patent
Mathur et al.

(10) Patent No.: US 8,661,453 B2
(45) Date of Patent: Feb. 25, 2014

(54) MANAGING HEALTHCARE INFORMATION IN A DISTRIBUTED SYSTEM

(75) Inventors: Alok Mathur, Alpharetta, GA (US); James K. Lassetter, Scottsdale, AZ (US); Andy Piccolo, Gainesville, GA (US); Saurabh Mathur, Cumming, GA (US); Robert Connely, Roswell, GA (US)

(73) Assignee: Medicity, Inc., Salt Lake City, UT (US)

( * ) Notice: Subject to any disclaimer, the term of this patent is extended or adjusted under 35 U.S.C. 154(b) by 137 days.

(21) Appl. No.: 13/280,287

(22) Filed: Oct. 24, 2011

(65) Prior Publication Data

US 2012/0102502 A1    Apr. 26, 2012

Related U.S. Application Data

(60) Provisional application No. 61/406,003, filed on Oct. 22, 2010.

(51) Int. Cl.
    *G06F 13/00*    (2006.01)
(52) U.S. Cl.
    USPC .......................................... 719/313; 719/318
(58) Field of Classification Search
    USPC ................................................. 719/313, 318
    See application file for complete search history.

(56) References Cited

U.S. PATENT DOCUMENTS

| | | | |
|---|---|---|---|
| 5,579,393 A | 11/1996 | Conner et al. | |
| 7,877,694 B2 * | 1/2011 | Antonelli et al. | 715/746 |
| 8,000,977 B2 * | 8/2011 | Achan | 705/2 |
| 8,140,613 B2 * | 3/2012 | Lum et al. | 709/201 |
| 2002/0016530 A1 | 2/2002 | Brown | |
| 2005/0010443 A1 | 1/2005 | Zammitt | |
| 2005/0159983 A1 | 7/2005 | Sullivan | |
| 2005/0268094 A1 | 12/2005 | Kohan et al. | |
| 2006/0248310 A1 | 11/2006 | Kavalam et al. | |
| 2009/0030936 A1 * | 1/2009 | Ordille et al. | 707/103 R |
| 2009/0132586 A1 | 5/2009 | Napora et al. | |
| 2009/0180398 A1 | 7/2009 | Lejeune | |
| 2010/0192125 A1 | 7/2010 | Son et al. | |

OTHER PUBLICATIONS

International Search Report, International Application No. PCT/US2011/057535, Jun. 28, 2012, 5 pgs.

* cited by examiner

*Primary Examiner* — Andy Ho
(74) *Attorney, Agent, or Firm* — Patent Law Works LLP

(57) ABSTRACT

A system and method for managing healthcare information is disclosed. The data servers each include a data manager that comprises a controller, a grid engine, applications, an application manager and a user interface engine. The controller manages the core functions and the transmission of data between data manager components. The grid engine manages information sent between data servers. The applications are applications that are created by the user or downloaded as third-party applications. The application manager manages the creation and communication between applications. The user interface engine generates user interfaces for displaying the applications and collecting clinical trial data.

20 Claims, 22 Drawing Sheets

MANAGING HEALTHCARE INFORMATION IN A DISTRIBUTED SYSTEM

CROSS-REFERENCE TO RELATED APPLICATIONS

This application claims priority under 35 USC §119(e) to U.S. provisional patent Application Ser. No. 61/406,003, entitled "System and Method for Managing Healthcare Information," filed Oct. 22, 2010.

BACKGROUND

1. Field of the Invention

The invention relates to managing healthcare information. In particular, the invention relates to a distributed system for managing healthcare information across different platforms.

2. Description of the Related Art

The exchange of electronic healthcare information over networks is increasing. The electronic healthcare information is exchanged between medical offices and other physicians, local hospitals and clinics, location and national labs and imaging centers, insurance payers, local pharmacies, public health and government agencies and patients. This type of collaboration requires the practice to engage in numerous healthcare transactions with many different people and organizations. These transactions include ordering and scheduling tests and obtaining results, referring and consulting on patients with other providers, obtaining authorization and filing claims with insurance payers and prescribing and refilling medications. Physicians and their staff are frequently on the phone, at the fax machine and on the Internet performing collaborative exchanges. Some of the cost associated with these exchanges would be reduced if more of the communications were performed electronically.

Previous attempts to overcome these problems suffer from deficiencies. For example, some physicians have created electronic medical records (EMRs), however, the physicians typically maintain an internal system and if they do exchange information it is only with hospitals, payers, labs and pharmacies. Thus, the physicians are missing an opportunity for a larger exchange of information.

Health information exchanges (HIEs) are appearing in many communities, however, they lack widespread acceptance and their focus is on creating comprehensive, patient-centric records and not on enhancing clinical workflow for physician practices.

Other solutions suffer from deficiencies that prevent them from being adopted by physicians. For example, most software is insufficient or too immature to meet the broad range of collaborative needs of a physician practice. In addition, the costs of adopting the technology, both for the licensing and the expense of re-engineering the practice, are often considered too great. Lastly, the existing systems fail to match the established workflow that the physicians and staff are accustomed to performing. As a result, the existing system must be restructured, which requires manual intervention by the staff to complete the process.

SUMMARY OF THE INVENTION

The technology described in the invention overcomes the deficiencies and limitations of the prior art at least in part by providing a system and method for managing healthcare information. The data manager allows users to control the application as they see fit by configuring the settings and downloading different applications to include as part of the data manager. The data manager is securely connected to other collaborative partners in the community and works with local and remote computer systems. In addition, because there are multiple data managers in the system that store different pieces of information, there is no risk of a system-wide failure.

In one embodiment, a rendezvous engine acts as an intermediate between data servers. The data servers each include a data manager that comprises a controller, a grid engine, applications, an application manager, and a user interface engine. The controller manages the core functions and the transmission of data between data manager components. The grid engine manages information sent between data servers. The applications are applications that are created by the user or downloaded as third-party applications. The application manager manages the creation and communication between applications. In one embodiment, the application manager includes an application module for creating applications, a certification module for certifying applications, a collaboration module for generating a list of data servers that communicate with the data server that includes the collaboration module, a contextual module for managing the interactions between the applications and a bridge module for managing the exchange of information between applications. The user interface engine generates user interfaces for displaying the applications and collecting clinical trial data.

BRIEF DESCRIPTION OF THE DRAWINGS

The invention is illustrated by way of example, and not by way of limitation in the figures of the accompanying drawings in which like reference numerals are used to refer to similar elements.

DETAILED DESCRIPTION OF THE PREFERRED EMBODIMENTS

Figure 1:
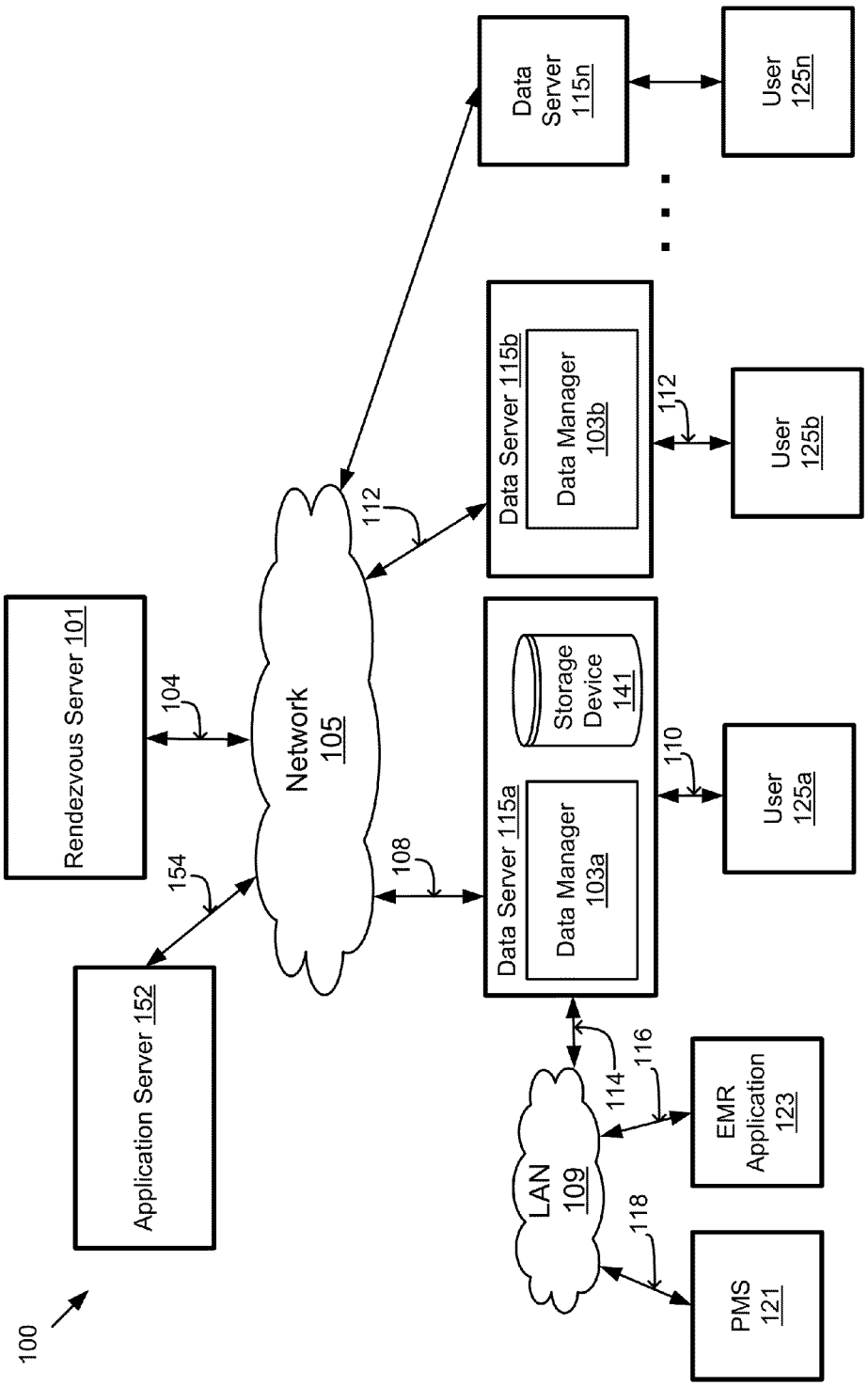
FIG. 1 is a high-level block diagram illustrating a system for managing data according to one embodiment of the invention.

A system and method for managing healthcare information are described below. In the following description, for purposes of explanation, numerous specific details are set forth in order to provide a thorough understanding of the invention. It will be apparent, however, to one skilled in the art that the technology described in the various example embodiments can be practiced without these specific details. In other instances, structures and devices are shown in block diagram form in order to avoid obscuring the invention.

Reference in the invention to "one embodiment," "an embodiment" or "an example embodiment" means that a particular feature, structure, or characteristic described in connection with the embodiment is included in at least one embodiment of the description. The appearances of the phrase "in one embodiment" in various places in the invention are not necessarily all referring to the same embodiment.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present embodiment of the invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the invention is not described with reference to any particular programming language. It will be appreciated that a variety of programming languages may be used to implement the teachings of the invention as described herein.

System Overview

FIG. 1 illustrates a block diagram of a system 100 for managing decentralized healthcare information according to one embodiment of the invention. In FIG. 1 and the remaining figures, a letter after a reference number, such as "115a" is a reference to the element having that particular reference number. A reference number in the text without a following letter, such as "115," is a general reference to any or all instances of the element bearing that reference number. In the illustrated embodiment, these entities are communicatively coupled via a network 105.

The illustrated description of a system 100 for managing healthcare information includes data servers 115a, 115b . . . 115n that are accessed by users 125a, 125b . . . 125n, practice management software (PMS) 121, an electronic medical records (EMR) application 123, an application server 152 and a rendezvous server 101. In the illustrated embodiment, these entities are communicatively coupled via a network 105. The data servers 115a, 115b . . . 115n in FIG. 1 are used by way of example. While FIG. 1 illustrates three data servers 115a, 115b . . . 115n, the description applies to any system architecture having one or more data servers. Data server 115a is coupled to the network 105 via signal line 108. A user 125a accesses the data server 115a via signal line 110. In one embodiment the data server 115a is a master data server 115a that manages the organization of some information for the other data servers 115n. Data server 115b is coupled to the network 105 via signal line 112. A user 125b accesses the data server 115b via signal line 120.

In one embodiment, the data server 115a is a hardware server, such as one powered by Medicity®. The data server 115a comprises a data manager 103a and a storage device 141. The data manager 103a manages healthcare information that is stored in the storage device 141 and controls how long the information persists in the storage device 141. The data server 115a is coupled to a local area network (LAN) 109 via signal line 114.

In one embodiment, the data server 115a communicates over the LAN to access the EMR application 123 via signal line 116 and to access the PMS 121 via signal line 118. The EMR application 123 is software for managing electronic medical records that are kept by an enterprise, such as a physician's office. The PMS is software for managing the day-to-day operations of a medical practice, such as tracking patients, scheduling appointments and managing billing including entering charges for services, coding the services and submitting claims out to insurance companies. Although only the EMR application 123 and PMS 121 are depicted in this illustration as being connected to the LAN 109, the data server 115a could communicate over the LAN to access other systems and devices. The data server 115 is described in greater detail below with reference to FIG. 2B.

The system 100 illustrates a distributed computing model where each data server 115 runs a data manager 103. Each data manager 103a exchanges information with other data managers 103n. A community of data managers 103n forms a grid, which is a transmission network that supports the transportation of information. The data manager 103a exchanges information with other data managers 103n in a secure manner by limiting access to information to specific members of the system 100. Specifically, a user 125a of the data manager 103a determines which other participants on the grid the user 125a wants to participate with, which eliminates the risk that others outside of the closed community will access the information.

The rendezvous server 101 manages the asynchronous communication of information between data servers 115a, 115b . . . 115n. The rendezvous server 101 accesses the network via signal line 104. Although only one rendezvous server 101 is illustrated, persons of ordinary skill in the art will recognize that multiple rendezvous servers 101 are possible. The rendezvous server 101 is described in greater detail with reference to FIG. 2A.

The application server 152 manages uploading, purchasing and downloading of applications by a user 125a of the data manager 103a. The applications are downloaded by other data managers 103n and incorporated into the data manager 103n. The applications are described in greater detail below with reference to FIG. 3B. In one embodiment, the application server 152 is stored on a master data server 115a. The application server 152 is coupled to the network 105 via signal line 154.

In one embodiment, the application server 152 processes purchases by communicating with the rendezvous server 101 to retrieve the user's 125n identity, billing the user 125n for the purchase, generating receipts and performing other functions known to those of ordinary skill in the art for completing a purchase. In one embodiment, the application server 152 distributes a percentage of the purchase price to the user that developed the application and keeps the rest of the purchase price as a service charge for maintaining an application store.

The network 105 is a conventional type, wired or wireless, and may have any number of configurations such as a star configuration, token ring configuration or other configurations known to those skilled in the art. Furthermore, the network 105 may comprise a local area network (LAN), a wide area network (WAN) (e.g., the Internet), and/or any other interconnected data path across which multiple devices may communicate. In yet another embodiment, the network 105 may be a peer-to-peer network. The network 105 may also be coupled to or includes portions of a telecommunications network for sending data in a variety of different communication protocols. In yet another embodiment, the network 105 includes Bluetooth communication networks or a cellular communications network for sending and receiving data such as via short messaging service (SMS), multimedia messaging service (MMS), hypertext transfer protocol (HTTP), direct data connection, WAP, email, etc.

Rendezvous Engine 200

Figure 2A:
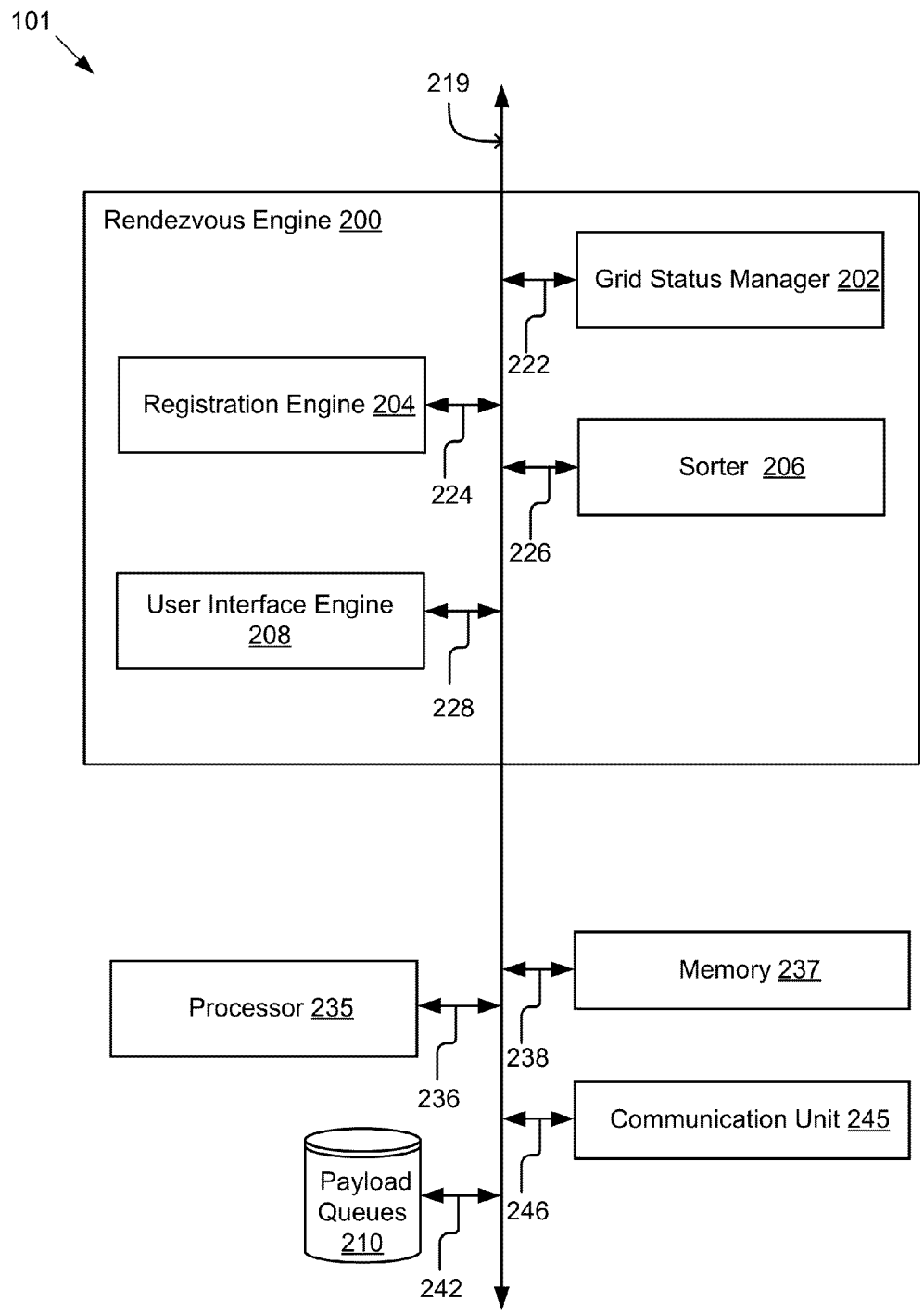
FIG. 2A is a block-diagram of a rendezvous engine according to one embodiment of the invention.

Referring now to FIG. 2A, the rendezvous server 101 comprises a rendezvous engine 200, a memory 237, a processor 235, a communication unit 245 and a storage device for storing payload queues 210 that are each coupled to the bus 219. The bus 219 may represent one or more buses including an industry standard architecture (ISA) bus, a peripheral component interconnect (PCI) bus, a universal serial bus (USB), or some other bus known in the art to provide similar functionality. In one embodiment, the rendezvous engine 200 comprises a grid status manager 202, a registration engine 204, a sorter 206 and a user interface engine 208. The rendezvous engine 200 is also discussed in U.S. Pat. No. 7,653,634, entitled "System for the Processing of Information between Remotely Located Healthcare Entities," filed Oct. 30, 2007 and U.S. Pat. No. 7,953,699, entitled "System for the Processing of Information between Remotely Located Healthcare Entities," filed Dec. 4, 2009, each of which is herein incorporated by reference.

The processor 235 comprises an arithmetic logic unit, a microprocessor, a general purpose controller or some other processor array to perform computations and provide electronic display signals to a display device. The processor 235 is coupled to the bus 220 for communication with the other components via signal line 236. Processor 235 processes data signals and may comprise various computing architectures including a complex instruction set computer (CISC) architecture, a reduced instruction set computer (RISC) architecture, or an architecture implementing a combination of instruction sets. Although only a single processor is shown in FIG. 2A, multiple processors may be included. The processing capability may be limited to supporting the display of images and the capture and transmission of images. The processing capability might be enough to perform more complex tasks, including various types of feature extraction and sampling. It will be obvious to one skilled in the art that other processors, operating systems, sensors, displays and physical configurations are possible.

The memory 237 stores instructions and/or data that may be executed by processor 235. The memory 237 is coupled to the bus 220 for communication with the other components via signal line 238. The instructions and/or data may comprise code for performing any and/or all of the techniques described herein. The memory 237 may be a dynamic random access memory (DRAM) device, a static random access memory (SRAM) device, flash memory or some other memory device known in the art. In one embodiment, the memory 237 also includes a non-volatile memory or similar permanent storage device and media such as a hard disk drive, a floppy disk drive, a CD-ROM device, a DVD-ROM device, a DVD-RAM device, a DVD-RW device, a flash memory device, or some other mass storage device known in the art for storing information on a more permanent basis.

The communication unit 245 transmits and receives data to and from the data servers 115n and the application server 152. The communication unit 245 is coupled to the bus 220 via signal line 246. In one embodiment, the communication unit 245 includes a port for direct physical connection to the data servers 115n, the application server 152 or to another communication channel. For example, the communication unit 245 includes a USB, SD, CAT-5 or similar port for wired communication with the user device 115. In another embodiment, the communication unit 245 includes a wireless transceiver for exchanging data with the data servers 115n, the application server 152 or any other communication channel using one or more wireless communication methods, such as IEEE 802.11, IEEE 802.16, BLUETOOTH® or another suitable wireless communication method.

In yet another embodiment, the communication unit 245 includes a cellular communications transceiver for sending and receiving data over a cellular communications network such as via short messaging service (SMS), multimedia messaging service (MMS), hypertext transfer protocol (HTTP), direct data connection, WAP, e-mail or another suitable type of electronic communication. In still another embodiment, the communication unit 245 includes a wired port and a wireless transceiver. The communication unit 245 also provides other conventional connections to the network for distribution of files and/or media objects using standard network protocols such as TCP/IP, HTTP, HTTPS and SMTP as will be understood to those skilled in the art.

The grid status manager 202 is software including routines for managing activity information received from the data managers 103n. In one embodiment, the grid status manager 202 is a set of instructions executable by the processor 235 to provide the functionality below for hosting a message queue for each data manager 103n and receiving and verifying data manager session requests. In another embodiment, the grid status manager 202 is stored in the memory 237 and is accessible and executable by the processor 235. In either embodiment, the grid status manager 202 is adapted for cooperation and communication with the processor 235 and other components of the data manager 103 via signal line 222.

The registration engine 204 is software and routines for registering users 125n for access to the data manager 103n. In one embodiment, the registration engine 204 is a set of instructions executable by the processor 235 to provide the functionality below for registering users. The registration engine 204 receives a username and password, generates a unique identifier that is associated with the data manager 103n and receives user preferences for the user interface generated by the data manager 103n, such as preferred screen font size, colors and how the applications are organized. In another embodiment, the registration engine 204 is stored in the memory 237 and is accessible and executable by the processor 235. In either embodiment, the registration engine 204 is adapted for cooperation and communication with the processor 235 and other components of the rendezvous engine 200 via signal line 224. In one embodiment, the registration engine 204 communicates with a master data manager 103a to coordinate registration. In another embodiment, the registration engine 204 is a component of the master data manager 103a.

The sorter 206 is software and routines for handling payloads from data managers 103. In one embodiment, the sorter 206 is a set of instructions executable by the processor 235 to put incoming payloads into the payload queue 210, identify the destination for each payload, place the new payloads from the payload queue 210 in the outbox for the destination data managers 103n via the communication unit 245 and deletes payloads from the payload queue 210 after receipt of a discard request.

Data Manager 103

Figure 2B:
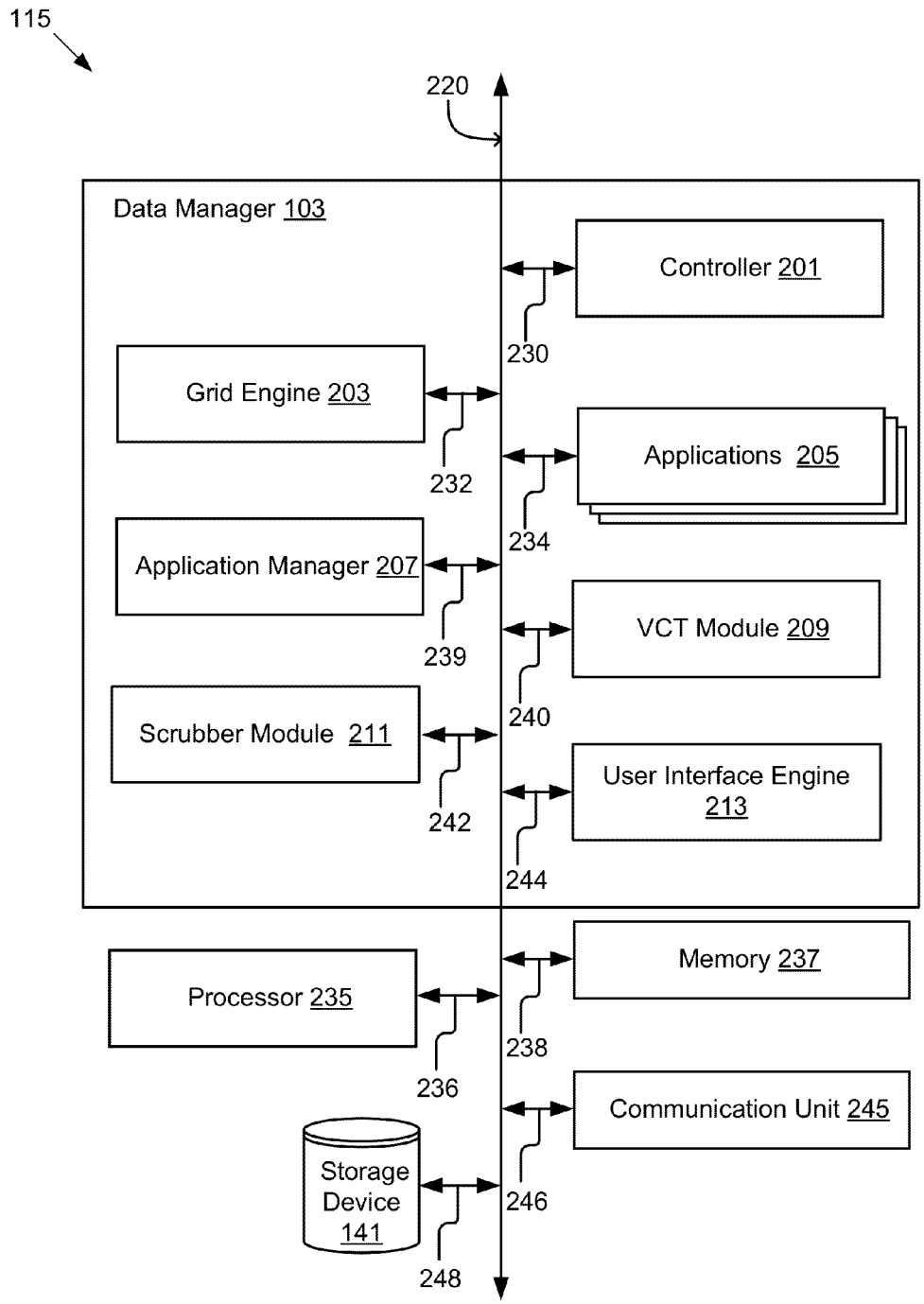
FIG. 2B is a block diagram of the data manager according to one embodiment of the invention.

Referring now to FIG. 2B, the data server 115 comprises a data manager 103, a memory 237, a processor 235, a communication unit 245 and a storage device 141 that are each connected to the bus 220. Those skilled in the art will recognize that some of the components of the data server 115 have the same or similar functionality to the components of the rendezvous server 101 so descriptions of these components will not be repeated here. For example, the processor 235, memory 237, bus 220 and communication unit 245 are similar to the processor 235, memory 237, bus 219 and communication unit 245, respectively.

In one embodiment, the data manager 103 comprises a controller 201, a grid engine 203, applications 205, an application manager 207, a Virtual Care Team (VCT) module 209, a scrubber module 211 and a user interface engine 213.

The controller 201 is software including routines for managing the core functions of the data manager 103 and for transmitting data to the different components. In one embodiment, the controller 201 is a set of instructions executable by the processor 235 to provide the functionality below for managing data. In another embodiment, the controller 201 is stored in the memory 237 and is accessible and executable by the processor 235. In either embodiment, the controller 201 is adapted for cooperation and communication with the processor 235 and other components of the data manager 103 via signal line 230.

In one embodiment, the controller 201 performs core functions by listening for data by listening to ports, scanning folders, etc.; inserting data into locations such as a TCP port, folders, etc.; parsing by converting incoming data into objects, such as Java objects; analyzing by examining objects to determine actions; saving data by creating a new topic or adding to a topic that is saved in the data storage 141; formatting by rendering data into the required format, such as by mapping, translating and grouping; sending packages of information for distribution and notifying by, for example, sending an email or a Web alert in response to an event occurring.

The grid engine 203 is software including routines for managing healthcare information on the data server 101. In one embodiment, the grid engine 203 is a set of instructions executable by the processor 235 to provide the functionality below for storing objects in the storage device 141, generating and encrypting payloads, generating a queue for outbound payloads, uploading payloads to the rendezvous engine 200, downloading payloads from the rendezvous engine 200, generating a queue for inbound payloads, decrypting and processing received payloads, executing commands from a master data manager 103a and performing maintenance activities. In another embodiment, the grid engine 203 is stored in the memory 237 and is accessible and executable by the processor 235. In either embodiment, the grid engine 203 is adapted for cooperation and communication with the processor 235 and other components of the data manager 103 via signal line 232.

In one embodiment, the storage device 141 includes a node warehouse and a topic warehouse. The node warehouse stores identifiers for the other data managers 103n (i.e. other nodes in the system 100) and information for authenticating data requests from the nodes, such as public key infrastructure (PKI) information. The storage device 141 is coupled to the bus 220 via signal line 248.

The topic warehouse stores topic objects that include topic attributes and capsules. In one embodiment, the topic attributes include an identifier (e.g. a universally unique identifier (UUID) that is associated with open source software), a list of participants, a creation date, a last modified date, a description and a type. Capsules are serialized objects that are stored as name/value pairs. In one embodiment, a capsule includes an identifier (e.g. HL7, original HL7, doctor, patient, audit), a description and information particular to the type of information in the capsule, such as information about a test, a department, a doctor, a topic status, a node ID, patient information and audit information. Capsules support many data formats including Health Level Seven (HL7), eXtensible Markup Language (XML), Portable Document Format (PDF), Tagged Image File Format (TIFF), WAVeform audio file (WAV), Digital Imaging and Communications in Medicine (DICOM) and Moving Picture Experts Group (MPEG). Persons of ordinary skill in the art will recognize that other data formats are possible. The grid engine 203 transmits the topics to any other data manager 103n in the system 100. When a data manager 103n makes a change to a copy of the topic, the grid engine 203 transmits the copy to the other data managers 103n to update their copy of the topic.

Figure 3A:
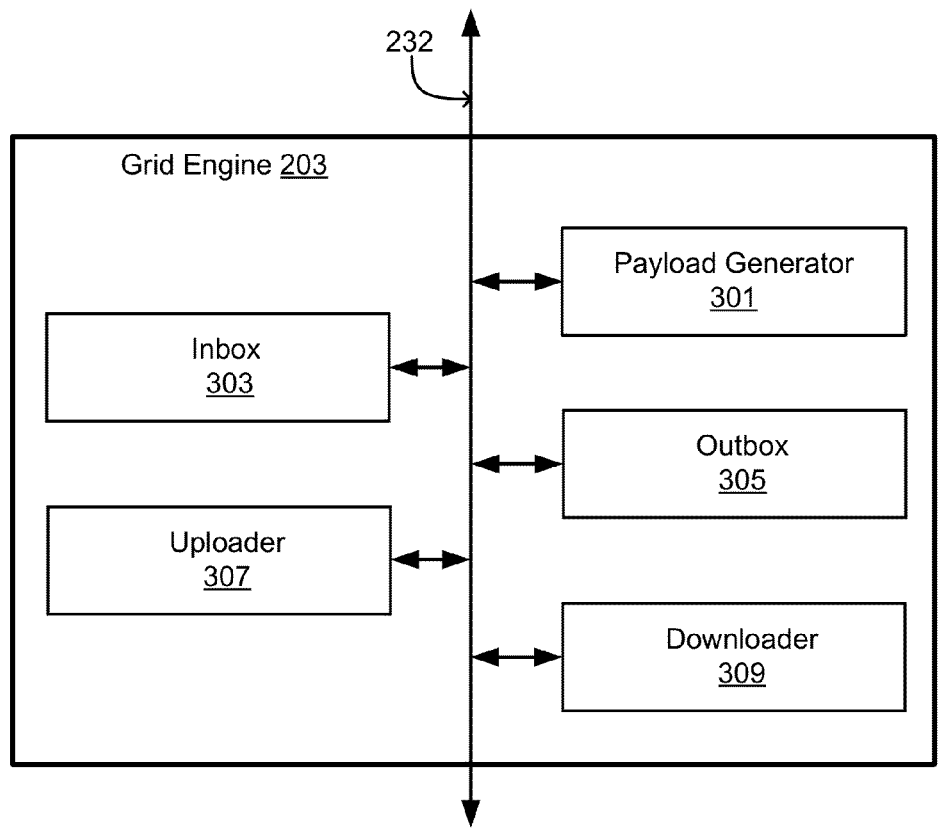
FIG. 3A is a block diagram of the grid engine according to one embodiment of the invention.

Turning now to FIG. 3A, a more detailed embodiment of the grid engine 203 is illustrated. The grid engine 203 comprises a payload generator 301, an inbox 303, an outbox 305, an uploader 307 and a downloader 309. The payload generator 301 performs authentication functions and generates payloads. In one embodiment, the payload generator 301 generates public/private key pairs, stores the private key in the data storage 141 and transmits the public key to the other data managers 103n that have access to the payloads.

The payload generator 301 generates a payload that includes the topic object. In one embodiment, the payload includes a class handler, a payload type, topic participants, a payload topic, a payload identifier, an original agent identifier, capsules and topics. The class handler is used to activate the grid engine 203 of the data manager 103n that receives the payload. The payload type is a topic or capsule. The topic participants is a list of data managers 103n that have access to the topic. The payload capsule is a list of the identifier for the capsules contained in the payload. The payload identifier is a unique identifier for identifying the payload, such as a UUID. The origin agent identifier is the unique identifier of the data manager 103 that created the original payload.

Once the payload generator 301 creates the payload, the payload generator 301 generates a payload header that includes the identifier for the recipient data manager 103n and encrypts the payload with a public key of the recipient data manager 103n. In one embodiment, the payload generator 301 encrypts the payload by encrypting the topic attributes and the capsules with a 2048-bit Advanced Encryption Standard (AES) symmetric key, incorporates a digital signature of the data manager 103 that creates the payload with a Hash-based Message Authentication Code (HMAC), and the payload is encrypted using a HyperText Transfer Protocol Secure (HTTPS).

The outbox 305 maintains an outbox queue. In one embodiment, the outbox 305 stores the payload created by the payload generator 301 in an outbox queue, periodically contacts the rendezvous engine 200, establishes a secure sockets layer (SSL), uploads the content of the message outbox queue and sends discard requests to the rendezvous engine 200 via the communication unit 245. The rendezvous engine 200 places the payload in the outbox for the destination data manager 103n. The designation data manager 103n downloads the payload, decrypts the AES key with its private key and uses the AES key to decrypt the payload.

The inbox 303 maintains a message inbox queue by downloading any new messages from the rendezvous engine 200 via the communication unit 245 and puts the new messages in the message inbox queue.

Applications 205

The applications 205 are software including routines for performing tasks. In one embodiment, the applications 205 are a set of instructions executable by the processor 235 for performing tasks. In another embodiment, the applications 205 are stored in memory 237 of the data server 115 and are accessible and executable by the processor 235. In either embodiment, the applications 205 are adapted for cooperation and communication with the processor 235, the storage device 141, the controller 201, the application manager 207, the user interface engine 213 and other components of the data server 115 via the signal line 226.

The applications 205 include any type of applications such as an enterprise application, an accounting application, a word processing application, a media application, etc. The applications are for performing tasks such as retrieving health care data of a patient, processing payments received from an insurance provider, authorizing payments, ordering labs, dictation software, maintaining a healthcare registry (e.g. bone marrow), receiving health check-up results of a patient from a lab, sending prescriptions to a drugstore, etc. In one embodiment, the applications 205 are developed by a user 125. In another embodiment, the applications 205 are third-party applications that are downloaded from an application server 152 and installed on the data server 115. The application server 152, for example, includes an application store that allows users to search, browse, purchase and download third-party applications.

Application Manager 207

The application manager 207 is software including routines for developing and managing the applications 205. In one embodiment, the application manager 207 is a set of instructions executable by the processor 235 to provide the functionality described below for developing and managing the applications 205. In another embodiment, the application manager 207 is stored in memory 237 of the data server 115 and is accessible and executable by the processor 235. In either embodiment, the application manager 207 is adapted for cooperation and communication with the processor 235, the storage device 141, the controller 201, the applications 205, the user interface engine 213 and other components of the data server 115 via the signal line 239. The application manager 207 is described in further detail with reference to FIG. 3B.

Figure 3B:
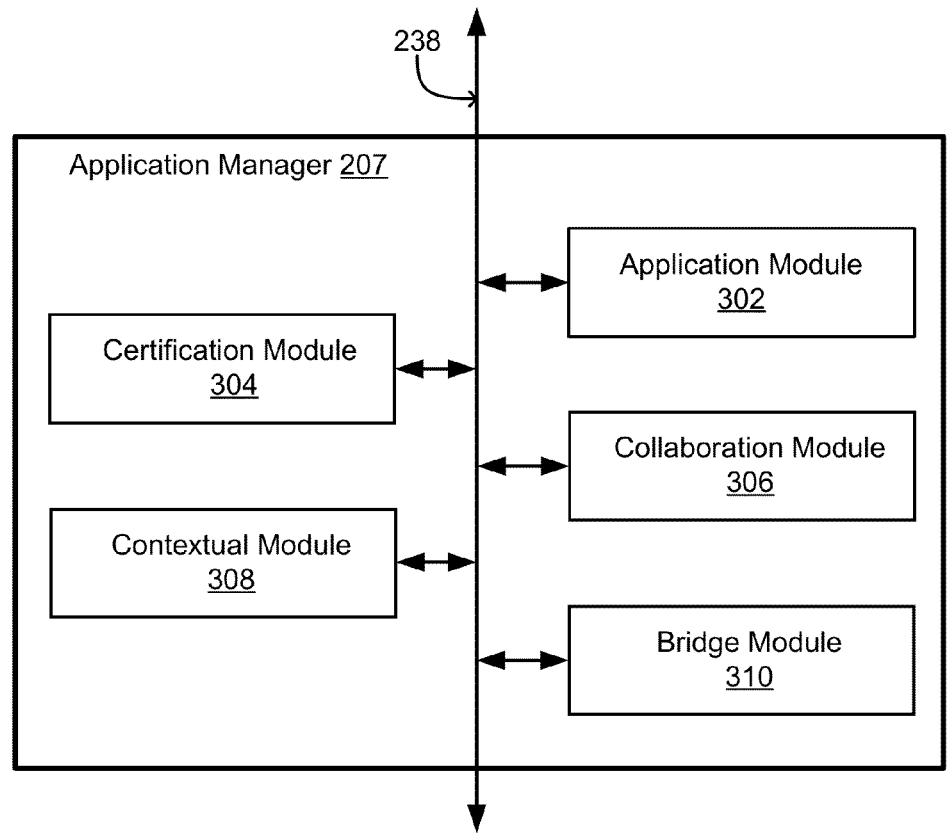
FIG. 3B is a block diagram of the application manager according to one embodiment of the invention.

FIG. 3B illustrates one embodiment of the application manager 207 in more detail. In this embodiment, the application manager 207 includes an application module 302, a certification module 304, a collaboration module 306, a contextual module 308, a bridge module 310.

The application module 302 is software including routines for allowing users 125 to develop and install applications 205 on the data server 115. The application module 302 receives a request submitted by the user 125 to develop a new application, install a third-party application, etc. from the controller 201. In one embodiment, the application module 302 includes a software development kit (SDK) comprising a set of development tools that allow users 125 to develop applications 205. In another embodiment, the application module 302 allows users 125 to download and install third-party applications 205 from an application server 152. In both embodiments, the application module 302 allows the users 125 to define preferences and rules for the applications 205. The application module 302 stores the rules and preferences in the storage device 141. In yet another embodiment, the application module 302 includes tools to develop application programming interfaces (APIs) to allow the data manager 103 to interact with third-party applications stored in the application server 152 or any other data servers 115n. In one embodiment, the application module 302 uses Java adapters to provide software developers with the tools for accessing different information platforms, such as the data servers 115n and local, state and national registries. The application module 302 transmits the newly created application to the application server 152 via the communication unit 245 to make it available to other users.

Examples of tools for accessing platforms include a journal API for creating, updating and accessing data in personal journals; a messaging API for accessing the secure messaging infrastructure to exchange information with other platforms; a physician directory API for accessing a global directory of physicians and other provides that are on the grid; a print service for accessing local printers; an International Classification of Disease (ICD) lookup for accessing ICD-9 diagnosis tables; a Current Procedural Terminology (CPT) lookup for accessing CPT procedural tables; a Practice Management (PM) bridge for accessing data from the MPS bridge for demographic, insurance and scheduling queries; an Electronic Medical Records driver for accessing clinical data and other data queries and enabling the insertion of results, reports, referrals and other information; a vocabulary mapping service for translating local terms to standardized terms (e.g. Systemized Nomenclature of MEDicine (SNOMED)); a formatting service for standardizing forms; a community search for searching a Health Information Exchange (HIE) for patient information; and a payer gateway for exchanging information with payers that make their services available in an electronic exchange.

The journal API is used to create a patient record. In one embodiment the journal API includes demographic information including name, date of birth and address for a patient; scheduling information including appointment type, date and time; clinical problems that are both current and historical for the patient; procedures or treatments for the patient; family history; social history that includes lifestyle, occupation, environmental health risks and patient demographics such as marital status, ethnicity and religion; advanced directives including wills, healthcare proxies and resuscitation wishes including both patient instructions and references to external documents; alerts such as allergies and adverse reactions; medications including current medications and relevant historical medication usage; immunizations including immunization status and historical information about past immunizations; medical equipment and any implanted or external devices; vital signs including trends over time and baselines; functional status including information about what is normal for the patient, deviations from normalcy (both positive and negative) and extensive examples; results including lab and procedure results and reports; encounters including past healthcare encounters including activity and location; and a plan of care including active, incomplete or pending activities for the patient including orders, appointments, procedures, referrals and services.

The certification module 304 is software including routines for certifying the applications 205 developed by the users 125. In one embodiment, the certification module 304 receives a message from the application module 302 that a new application has been developed by a user 125. The certification module 302 determines whether the new application is compatible with the applications 205 that are installed on the data server 115. For example, the certification module 304 determines whether the new application includes APIs to interact with the applications 205. In another embodiment, the certification module 304 certifies that the new application can be uploaded to an application server 152. The certification module 304 instructs the user interface engine 213 to generate a user interface that displays a message. In one embodiment, the message indicates that the new application is certified to be installed on the data server 115, uploaded to the application server 152, etc. In another embodiment, the message indicates that the new application is not certified and includes a list of issues that need to be resolved for the new application to be certified.

The collaboration module 306 is software including routines for generating a list of data servers 115n that communicate with the data server 115a. In one embodiment, the list includes the applications installed in each of the data servers 115n. The collaboration module 306 generates the list in response to receiving a request submitted by a user 125 to develop a new application. The user 125, for example, uses the list to develop APIs for the new application.

The contextual module 308 is software including routines for managing the interactions between the applications 205. The contextual module 308 receives a message from an application 205 when the application 205 performs a task. The contextual module 308 analyzes the task, for example, analyzes a request submitted by the user 125, the retrieved health care data of a patient, etc. The contextual module 308 determines if the analysis matches one or more rules or preferences that are defined for any other application installed on the data server 115. In response to determining a match with a rule or a preference of an application, the contextual module 308 transmits a notification to the application. The contextual module 308 is described in further detail with reference to FIG. 7.

The bridge module 310 is software including routines for managing the exchange of data between the applications 205 and the computing systems, for example, PMS 121, the EMR application 123, diagnostic devices (not shown), etc. that are locally connected to a data server 115. The bridge module 310 communicates data such as, queries, instructions, messages, health care data of a patient, etc. between the applications 205 and the local computing systems. The bridge module 310 converts the data into a format that is compatible with the requirements of the destination. For example, an application 205 generates a query for retrieving a list of patients with leukemia from the EMR application 123. The bridge module 310 converts the query into a HL7 standard and submits the query to the EMR 123. The bridge module 310 receives the list of patients from the EMR 123, converts the list into a PDF as requested by the application 205 and transmits it to the application 310. The bridge module 310 converts the data to HL7 standards, Continuity of Care Document (CCD), Continuity of Care Record (CCR), Structured Query Language (SQL), PDF or any other format or standard known to a person of ordinary skill in the art.

Virtual Care Team (VCT) Module 209

The Virtual Care Team (VCT) module 209 is software including routines for creating VCT records that are related to a specific patient and for collaborating with other data servers 115n. In one embodiment, the VCT module 209 is a set of instructions executable by the processor 235 to provide the functionality described below for creating VCT records and collaborating with other data servers 115n. In another embodiment, the VCT module 209 is stored in memory 237 of the data server 115 and is accessible and executable by the processor 235. In either embodiment, the VCT module 209 is adapted for cooperation and communication with the processor 235, the storage device 141, the controller 201, the user interface engine 213 and other components of the data server 115 via signal line 240.

A VCT record comprises health care data associated with a patient or a group of patients (for example, a family, colleagues, etc.). The health care data includes a patient identity (ID), demographic information, information related to a care team of the patient, insurance information, prescriptions, results, allergies, medical history, referrals, rules, preferences, etc. A care team of a patient is a group of data servers 115n (for example, a primary physician, a cardiologist, an insurance provider, etc.) that are associated with the health care of the patient. The VCT module 209 is described in further detail with reference to FIG. 3C.

Figure 3C:
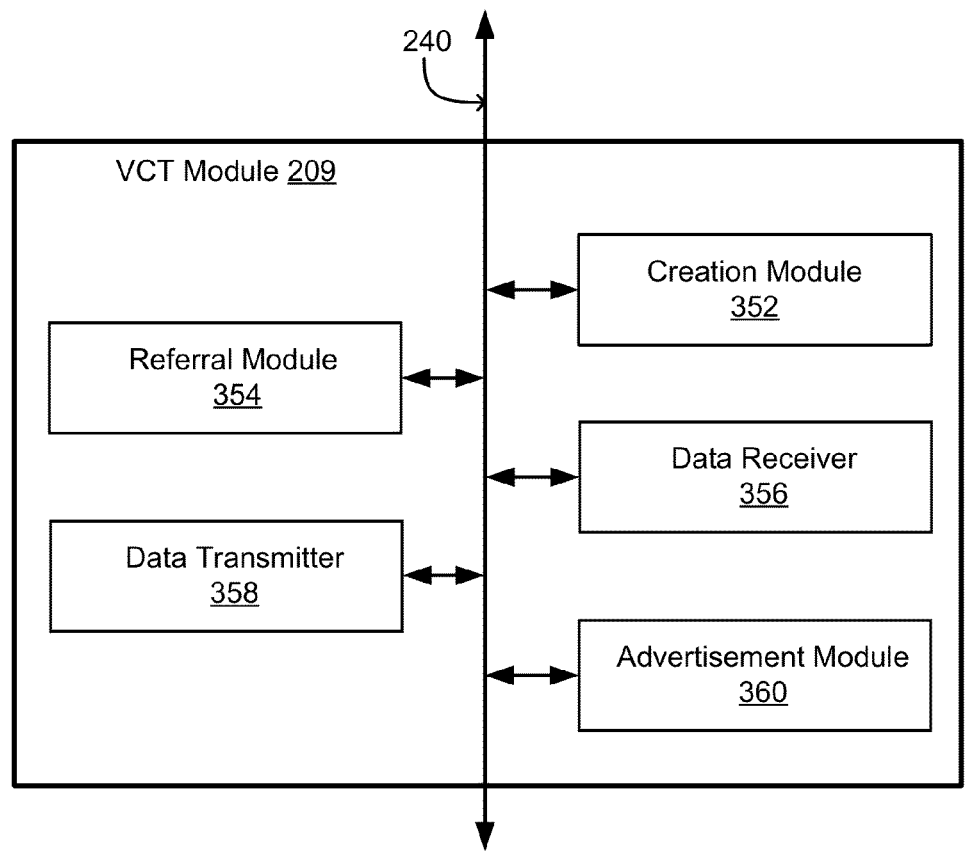
FIG. 3C is a block diagram of the virtual care team module according to one embodiment of the invention.

FIG. 3C illustrates one embodiment of the VCT module 209 in more detail. In this embodiment, the VCT module 209 includes a creation module 352, a referral module 354, a data transmitter 356, a data receiver 358 and an advertisement module 360.

The creation module 352 is software including routines for creating VCT records. The creation module 352 receives a request submitted by a user 125 for creating a VCT record (for example, a request submitted by a hospital administrator to create a VCT record for a new patient) from the controller 201. The creation module 352 generates a VCT record based on the information (for example, a registration form filled out by the patient, etc.) included in the request. In one embodiment, where the information included in the request in insufficient, the creation module 352 retrieves additional information about the patient from local databases such as the PMS 121, the EMR application 123, etc. In another embodiment the creation module 352 instructs the user interface engine 213 to generate a user interface requesting additional information from the user 125. The creation module 352 stores the VCT records in the storage device 141. The creation module 352 generates a VCT record that is helpful for both transmitting information to other data servers 115n and for transmitting a complete record to an application outside of the system 100.

The referral module 354 is software including routines for transmitting and receiving referrals for a patient to and from other data servers 115n. The referral module 354 identifies one or more data servers 115n for a patient from a directory of data servers in the storage device 141. In one embodiment, the referral module 354 identifies a data server 115b responsive to receiving a request submitted by a user 125a from the controller 201. The request, for example, is submitted by a primary care physician to identify a cardiologist for the patient. In another embodiment, the referral module 354 automatically identifies a data server 115b based on a patient's VCT record. For example, the referral module 354 determines that a patient does not have insurance coverage from the patient's VCT record. The referral module 354 then identifies an insurance provider for the patient. In yet another embodiment, the referral module 354 identifies a data server 115b for a patient responsive to receiving an instruction from an application 205. The referral module 354 identifies the data servers 115n for a patient corresponding to the information in the patient's VCT record. For example, the referral module 354 identifies a clinic located within five miles of the patient's house, a neurologist covered by the patient's insurance provider, etc.

The referral module 354 instructs the controller 201 to transmit a referral to the data server 115b. The instruction includes a copy of the patient's VCT record and information such as an identification of the data server 115b, methods to communicate with the data server 115b, etc. The referral module 354 updates the VCT record of the patient by adding the data server 115b to the care team of the patient. In one embodiment, the referral module 354 updates the VCT record of the patient in response to receiving an acknowledgment from the data server 115b.

The referral module 354 also receives referrals transmitted by other data servers 115n from the controller 201. The referral module 354 retrieves the copy of the patient's VCT record from the referral and assigns a patient ID that is local to the data server 115a. The referral module 354 then creates a link between the local patient ID and the patient ID present in the VCT record. The referral module 354 updates the copy of the patient's VCT record with the link and stores it in the storage device 141. The referral module 354 also instructs the controller 201 to transmit the link to the data servers 115n from which the referral was received. The referral module 354 is described in further detail with reference to FIG. 8A.

The data receiver 356 is software including routines for receiving new health care data associated with a patient from the controller 201. In one embodiment, the data receiver 356 receives new health care data submitted by a user 125. For example, the data receiver 356 receives the blood pressure level of a patient submitted by a nurse. In another embodiment, the data receiver 356 receives health care data from a computing system that is locally connected to the data server 115a. For example, the data receiver 356 receives scan images of a patient's shoulder from an MRI scanner that is connected to the data server 115a. In yet another embodiment, the data receiver 356 receives new health care data transmitted by other care team members of the patient, for example, prescriptions, updated insurance coverage plan, etc. In this embodiment, the data receiver 356 determines whether the new health care data is required by the data server 115a based on rules and preferences stored in the storage 141. For example, a cardiologist requires blood test results of a patient but not a physical therapist. In one embodiment, the data receiver 356 instructs the user interface engine 213 to generate a user interface that displays the new health care data. In this embodiment, a user 125, (for example, a physician, a nurse, etc.) selects the new health care data required for the data server 115a. The data receiver 356 retrieves the VCT record of the patient and updates it with the new health care data.

In one embodiment, the data receiver 356 performs reconciliation of new data that includes conflicting information. For example, the new information is demographic information that does not match any patient data in the storage device 141. The data receiver 356 determines different patients that might match the demographic information, for example, the data receiver 356 identifies patients that match the demographic information if the numbers in the data of birth are transposed or the name "Jon" is replaced with "John." The data receiver 356 saves the rule for correcting the conflicting information in the storage device 141. In one embodiment, the data receiver 356 transmits the corrected data to the care team member that submitted the conflicting information via the communication unit 245 for confirmation. If the same conflicting information is received in the future, the data receiver 356 corrects the information using the same rule.

The data transmitter 358 is software including routines for transmitting health care data associated with a patient to the patient's care team members via the communication unit 245. The data transmitter 358 receives new health care data associated with a patient from the data receiver 356. The data transmitter 358 identifies the patient's care team members from the VCT record. The data transmitter 358 then instructs the communication unit 245 to transmit the new health care data to the patient's care team members. In one embodiment, prior to instructing the communication unit 245, the data transmitter 358 formats the new health care data based on the preferences of each of the care team members. In another embodiment, the data transmitter 358 determines whether the new health care data can be transmitted to the care team members based on the rules (for example, care team member preferences, patient's privacy rules, HIPAA compliance, etc.) present in the patient's VCT record.

The advertisement module 360 is software including routines for advertising a data server 115a. The advertising module 360 generates advertisements that include a unique identifier associated with the data server 115a, such as a UUID and instructs the controller 201 to transmit them to other data servers 115n. The advertisement includes the information about the data server 115a such as, health care services provided by the data server 115a, a list of physicians, a list of insurance plans that cover the services provided by the data server 115a, location, etc. The advertisements are advantageous as, for example, the other data servers 115n transmit referrals to the data server 115a based on these advertisements.

Scrubber Module 211

The scrubber module 211 is software including routines for identifying individuals for a study, such as a clinical trial and for scrubbing patient data of identifying information. In one embodiment, the scrubber module 211 is a set of instructions executable by the processor 235 to provide the functionality described below for scrubbing identifying information in response to a request from an application 205. In another embodiment, the scrubber module 211 is stored in memory 237 of the data server 115 and is accessible and executable by the processor 235. In either embodiment, the scrubber module 211 is adapted for cooperation and communication with the processor 235, the storage device 141, the controller 201, the applications 205, the user interface engine 213 and other components of the data server 115 via the signal line 242. The scrubber module 211 is described in further detail with reference to FIG. 3D.

Figure 3D:
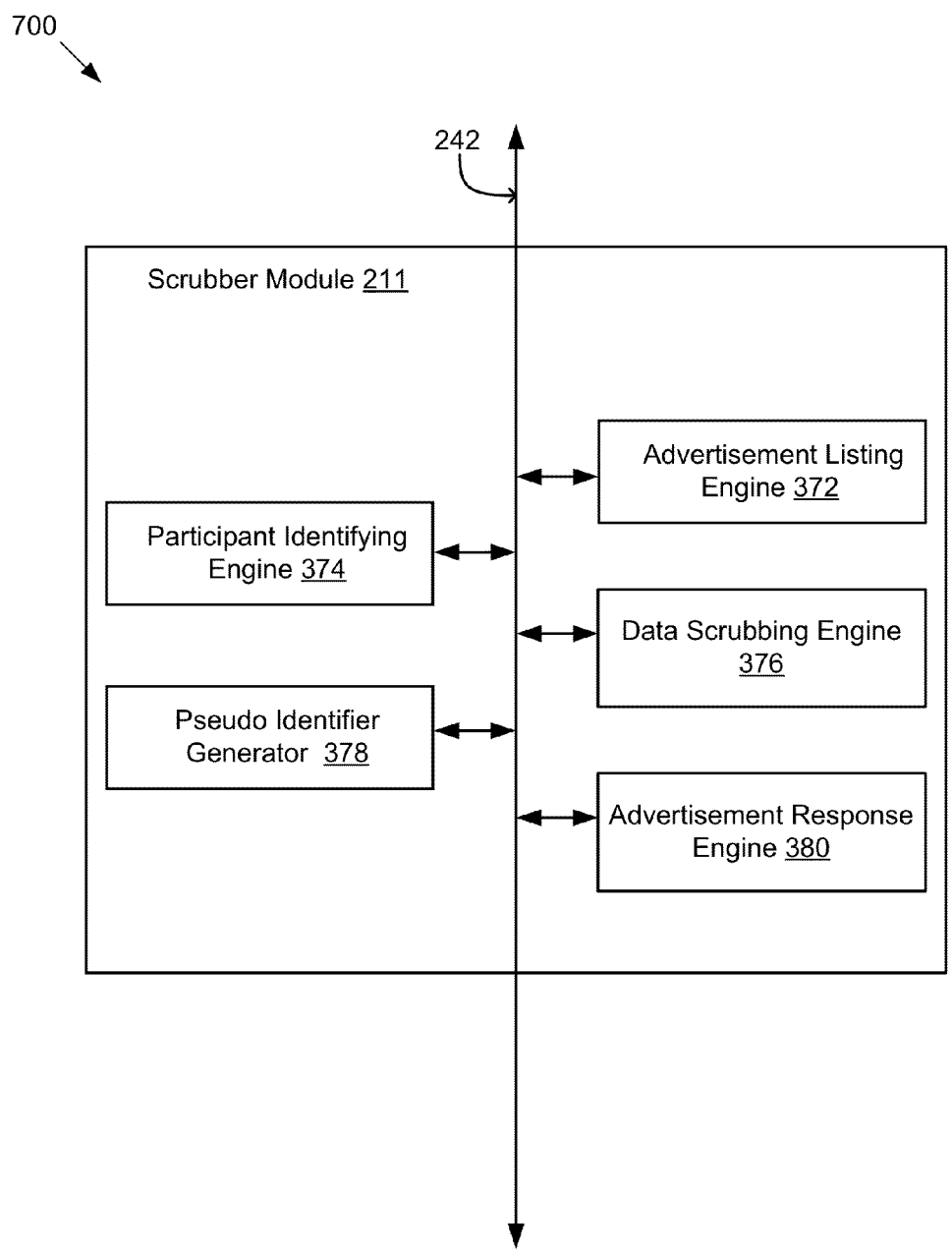
FIG. 3D is a block diagram of the scrubber module according to one embodiment of the invention.

Referring now to FIG. 3D, one embodiment of the scrubber module 211 is shown in more detail. FIG. 3D is a block diagram of the scrubber module 211 that includes an advertisement listing engine 372, a participant identifying engine 374, a data scrubbing engine 376, a pseudo identifier generator engine 378 and an advertisement response engine 380 that are each coupled to signal line 242.

The advertisement listing engine 372 registers an advertisement for recruiting potential participants for a study. The advertisement listing engine 372 receives a request for potential participants for a study from an organization. The organization is any group that uses medical information, such as a government health organization (e.g. the CDC), an insurance company and a clinical research organization (e.g. a hospital).

The request includes an identifier such as a name for the study and patient factors for identifying potential participants for the study. For example, a clinical research organization uses the scrubber module 211 to identify a number of individuals that are available for a study to test a medication for a health condition where the patients are in a particular age group and have responded adversely to a different medication. The clinical research organization places an advertisement that includes input data for identifying the participants. The input data relates to a diagnosis, medication, lab results, gender, age, location, previous medical history such as previous illnesses, a history of illnesses and other factors that are relevant to the study. In one embodiment, the advertisement listing engine 372 transmits the request to the participant identifying engine 374 for an immediate identification of potential participants for the study. In another embodiment, the participant identifying engine 374 stores the request in the storage device 141 for identification of potential participants for the study at a later time The participant identifying engine 374 identifies potential participants for a study based on the advertisement from an organization that is received from the advertisement listing engine 372. The participant identifying engine 374 identifies individuals based on matching the input data with patient data and medical records. In one embodiment, information for the identified individuals is transmitted to the data scrubbing engine 376. In another embodiment, the number of identified individuals that match is transmitted to the advertisement response engine 380.

The data scrubbing engine 376 modifies patient data to scrub it of identifying aspects. In one embodiment the data scrubbing engine 376 receives a request from an application 205 to scrub patient data. For example, the patient data includes data related to an admission of a patient or a lab event. In another embodiment, the data scrubbing engine 376 receives the individuals that match the advertisement from the participant identifying engine 374. The data scrubbing engine 376 receives patient data from a master patient index that is part of the data storage 141 or stored in another location, such as part of the EMR application 123. In one embodiment, the data scrubbing engine 376 modifies identifying information by removing demographic data. Identifiable demographic data includes name, address, birth date, ethnicity, government issued numbers such as a social security number and operational patient numbers such as a patient identifier. In another embodiment, the data scrubbing engine 376 modifies patient data by replacing the identifiable demographic data. For example, the data scrubbing engine 376 replaces the birth date with the age of the individual or transposes the digits for the birth date.

The data scrubbing engine 376 requests a pseudo identifier from the pseudo identifier generator engine 378. The pseudo identifier generator engine 378 generates a pseudo identifier for a patient. The data scrubbing engine 376 receives the pseudo identifier from the pseudo identifier generator engine 378 and associates the pseudo identifier with the patient by storing the pseudo identifier in the storage device 141.

In another embodiment, the data scrubbing engine 376 associates the pseudo identifier with the patient by storing the pseudo identifier with patient data in the master patient index. The data scrubbing engine 376 transmits the pseudo identifier and other data to the application 205 that requested the scrubbing or to the advertisement response engine 380. Therefore, the pseudo identifier is used by an organization to retrieve medical records of person without revealing the identity of the person. Also, because the pseudo identifier is a static identifier that is consistently associated with the same patient, the organization that requests the pseudo identifier tracks the same person over time. For example, a clinical research company uses the scrubber module 211 for a study for the same person over a period of 5 years.

The advertisement response engine 380 responds to an advertisement for recruiting potential participants for a study. The advertisement response engine 378 receives a number of patients that match the input data from the participant identifying engine 374 or scrubbed information from the pseudo identifier generator 378. In one embodiment, the advertisement response engine 380 notifies a provider of care that the individuals are identified as potential participants for the study. In another embodiment, the advertisement response engine 380 sends basic statistics to the organization that requested the potential participants. For example, the advertisement response engine 380 informs the organization that a specific number of potential participants have been identified by the participant identifying engine 372.

User Interface Engine 213

The user interface engine 213 is software including routines for generating a user interface in response to instructions received from the other data manager 103 components. In one embodiment, the user interface engine 213 is a set of instructions executable by the processor 235 to provide the functionality described below for generating a user interface for applications 205, the VCT module 209 or the scrubber module 211. In another embodiment, the user interface engine 213 is stored in memory 237 of the data server 115 and is accessible and executable by the processor 235. In either embodiment, the scrubber module 211 is adapted for cooperation and communication with the processor 235, the storage device 141, the applications 205, the user interface engine 213 and other components of the data server 115 via the signal line 242. The user interface engine 213 is described in further detail with reference to FIGS. 4A-4H.

Figure 4A:
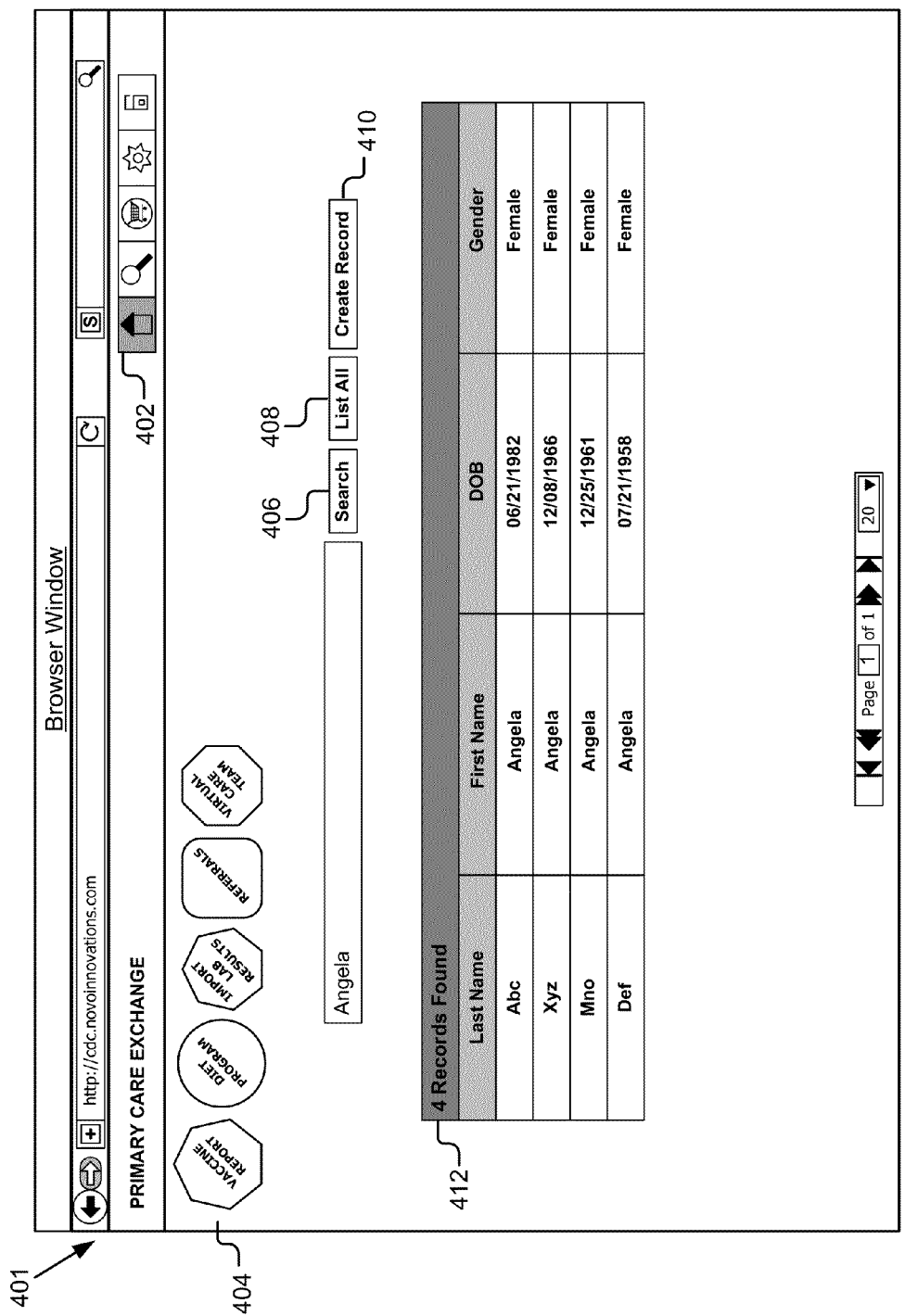
FIG. 4A is a graphical illustration of a user interface for accessing a patient record according to one embodiment of the invention.

Turning now to user interface engine 213, FIG. 4A is a graphic representation of a user interface 401 that is generated by the user interface engine 213 for accessing at least one patient record. In this example, the user interface 401 displays a homepage 402 of a medical office website for healthcare providers of that medical office. The homepage 402 includes icons 404 of underlying composite applications that are installed by a user to meet his or her unique needs. A user searches for a patient record by typing a first name of the patient, a last name of the patient or any combination thereof in the search box and hitting the search button 406 on the homepage 402. For example, typing "Angela" in the search box retrieves a list 412 of patients whose first name includes Angela. In addition, the homepage 402 includes a List All 408 button that, when selected displays the entire list of available patient records and a Create Record 410 button that, when selected, displays a user interface for creating a record for a new patient.

Figure 4B:
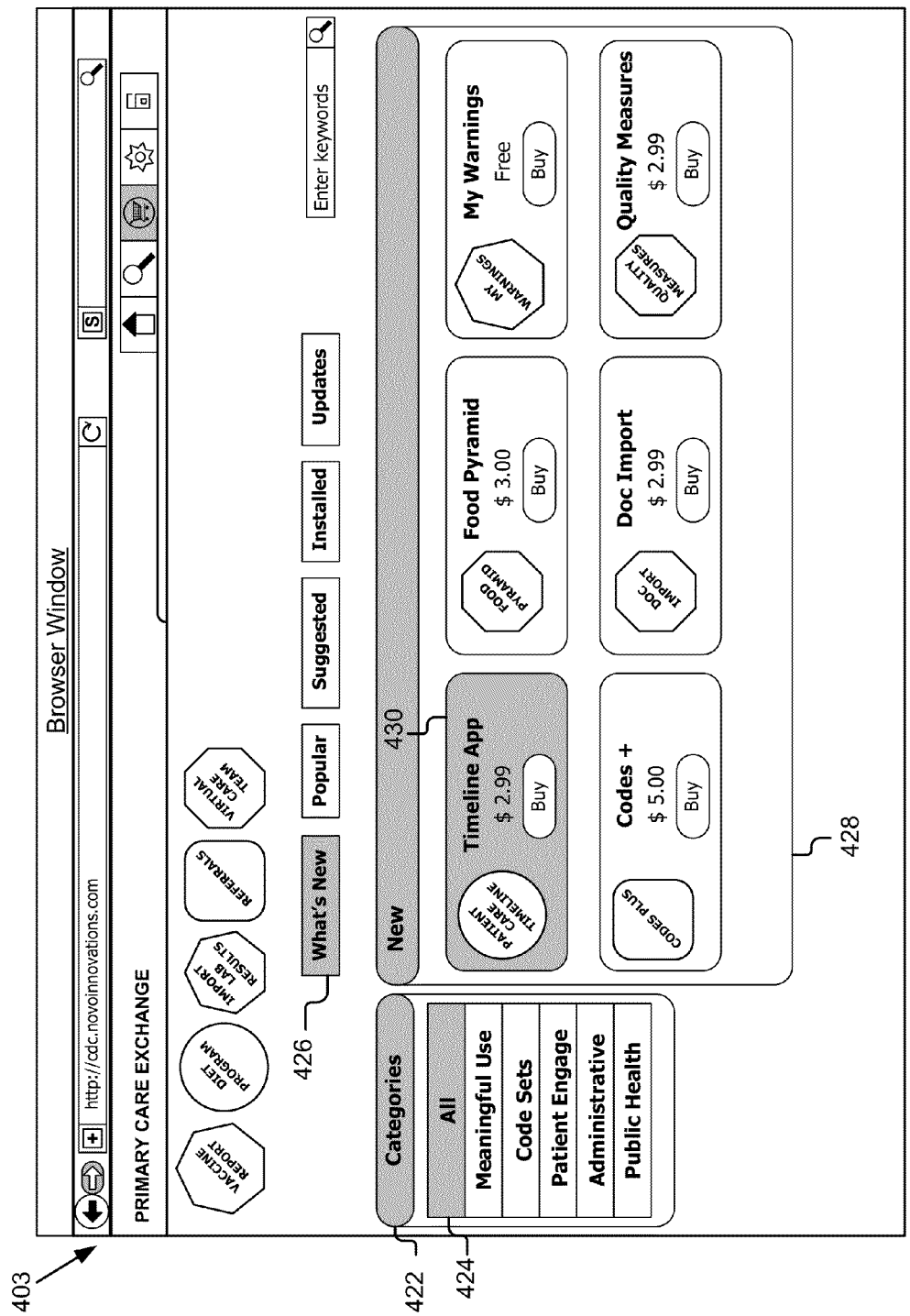
FIG. 4B is a graphical illustration of a user interface for viewing an application store according to one embodiment of the invention.

FIG. 4B is a graphic representation 403 of a user's view of an application store that is hosted by the application server 152. In this embodiment, the application store includes a categories icon 422 by which the user can view and select the type of applications to install. In addition to the categories icon 422, the application store lists the applications belonging to a particular type under sections such as popular applications, suggested applications, installed applications, updates to installed applications and new applications. In this example, the user selects the all icon 424 and selects the "what's new" tab 426. A sub-section 428 opens up that lists all the applications under the "what's new" tab 426 and the user chooses to buy the Timeline Application 430. In another embodiment, at least one of the applications listed is free to be installed by the user. In yet another embodiment, the applications listed in the application store are developed by third-party vendors.

Figure 4C:
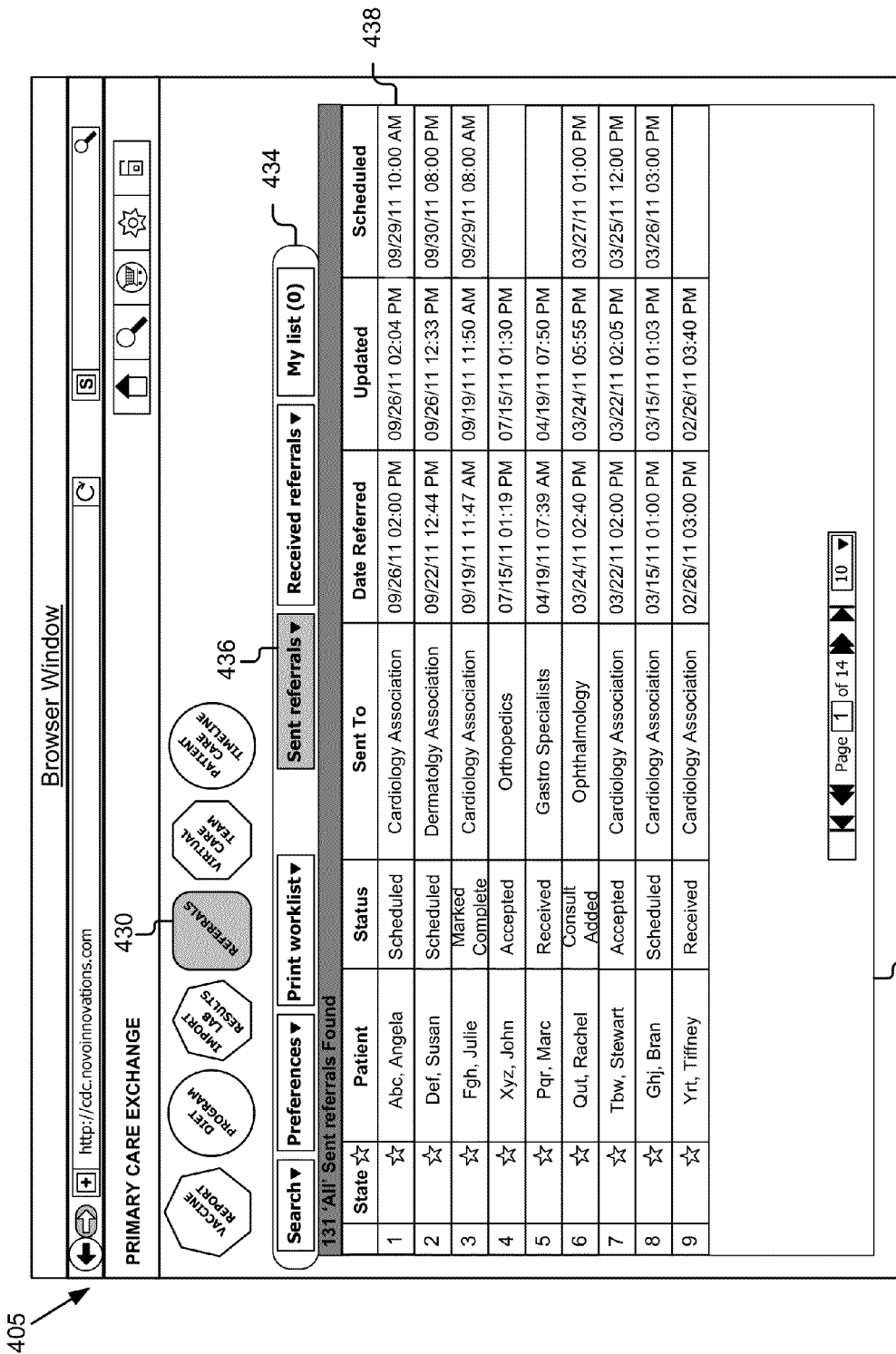
FIG. 4C is a graphical illustration of a user interface for viewing the functionality offered by the referral application according to one embodiment of the invention.

FIG. 4C is a graphic representation 405 of a user's view of the functionality offered by the referrals application 430 including sending and receiving of patient referrals. In this embodiment, the referrals application 430 displays a worklist 432 comprising the patient referrals 438 that were sent by the user in response to the user selecting the sent referrals 436 option. In another embodiment, the options present in the header 434 includes a drop down box to illustrate different categories in order to narrow down the referrals the user is interested in. For example, under the sent referrals 436 option, the user can choose to view referrals that are completed, in progress, denied and not yet accepted ones separately if interested. Each patient referral 438 comprises the patient name, status of the referral, the department or institution the referral is sent to and date and time of the referral, update and schedule. The user interface engine 213 allows the user to configure the display of the referral information 438 and other features of the display.

Figure 4D:
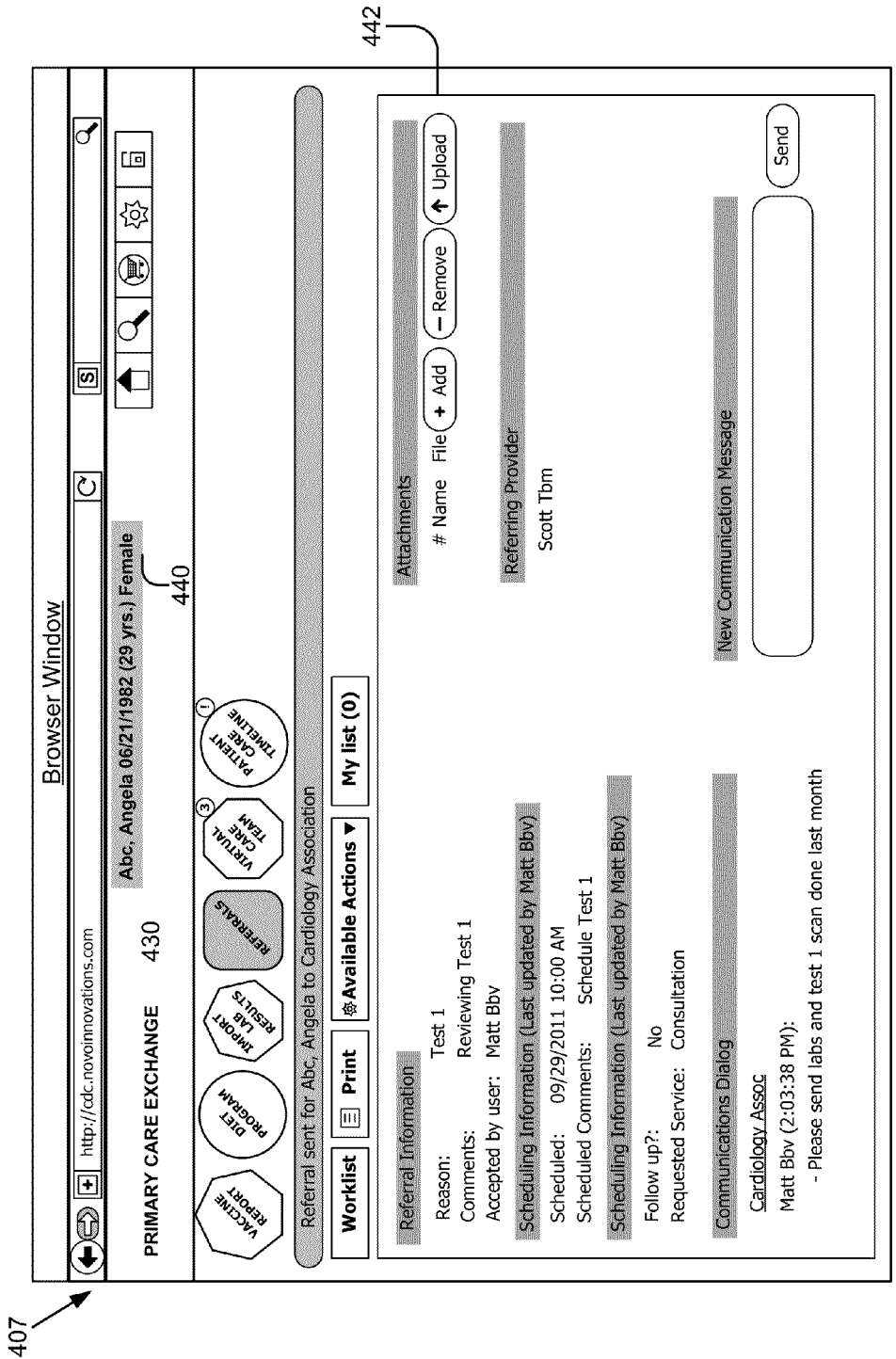
FIG. 4D is a graphical illustration of a different embodiment of a user interface for viewing the functionality offered by the referral application according to one embodiment of the invention.

FIG. 4D is another graphic representation 407 of a user's view of the functionality offered by the referrals application 430 in response to clicking on a patient referral 438 in FIG. 4C. In this embodiment, the list of underlying composite applications displayed near the top of the webpage change in their appearance visually at least in part to reflect the medical record of the patient 440 associated with the patient referral 438 from FIG. 4C. The referral application 430 includes the accompanying referral information 442 which lists the referring provider, referral details, scheduling information and any messages exchanged between the referring provider and the referred provider pertaining to the patient treatment.

Figure 4E:
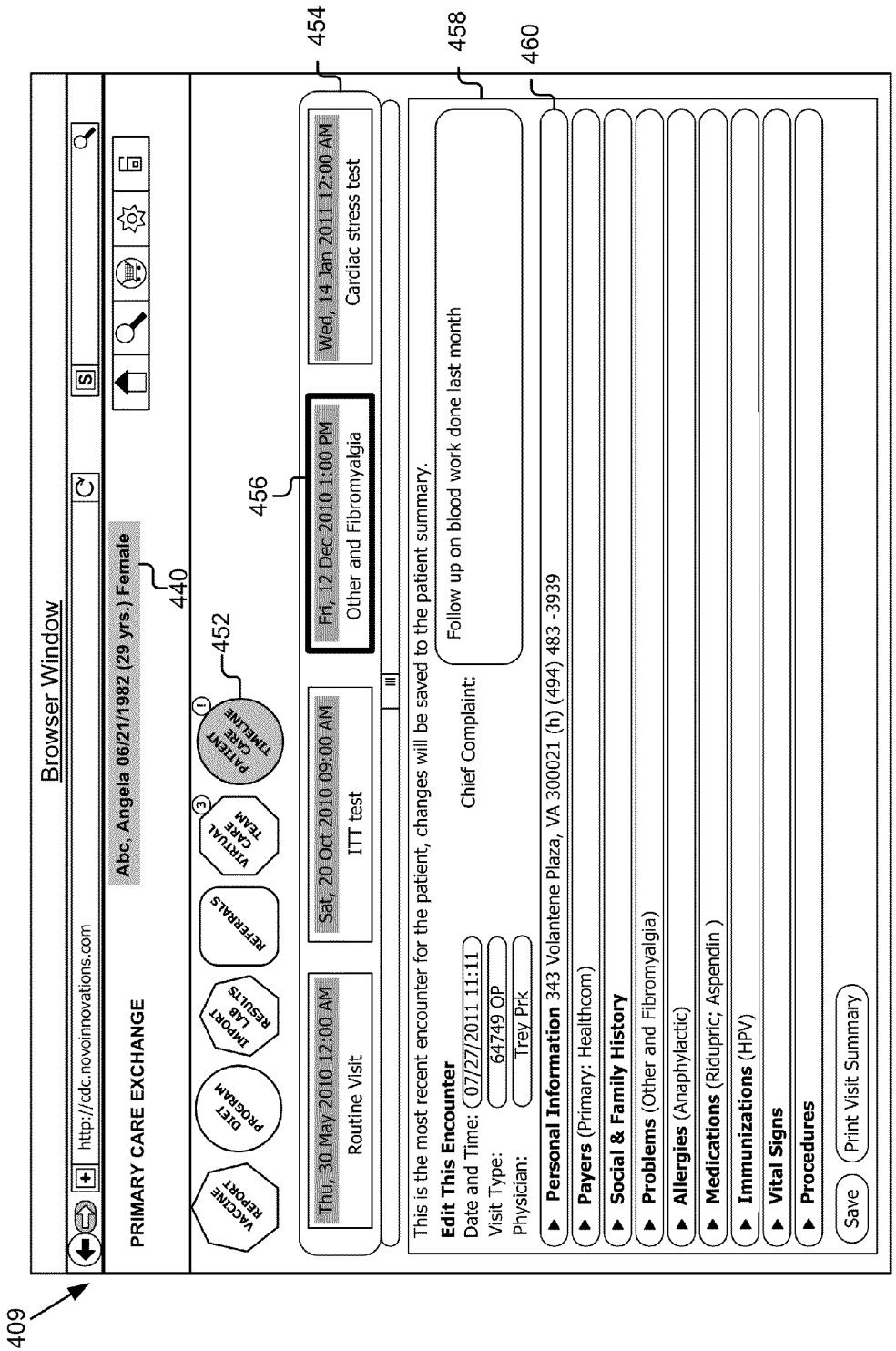
FIG. 4E is a graphical illustration of a user interface for viewing a timeline according to one embodiment of the invention.

FIG. 4E is a graphic representation 409 of a user's view of the functionality offered by the patient care timeline app 452. Graphic representation 409 displays a sliding list 454 of encounters with the patient 440 including routine visits, lab tests and checkups from at least one medical institution. Upon selecting one such encounter 456, the patient care timeline application 452 displays a sub section 458 listing the details of that particular encounter. The sub section 458 includes the physician's name, visit type, complaint, personal and medical information of the patient 440. Each information tab 460 associated with the patient 440, in response to clicking on it, expands to let the user view the information in detail and edit the information if needed. In another embodiment, the patient care timeline app 452 indicates visually to the user that at least one of the other underlying applications has important patient information which is pertinent to the patient care timeline application 452. For example, a highlighted exclamation mark on the patient care timeline application 452 in response to a highlighted numeral three on the virtual care team application is an indication that the two applications are ready to communicate with each other to reconcile patient record.

Figure 4F:
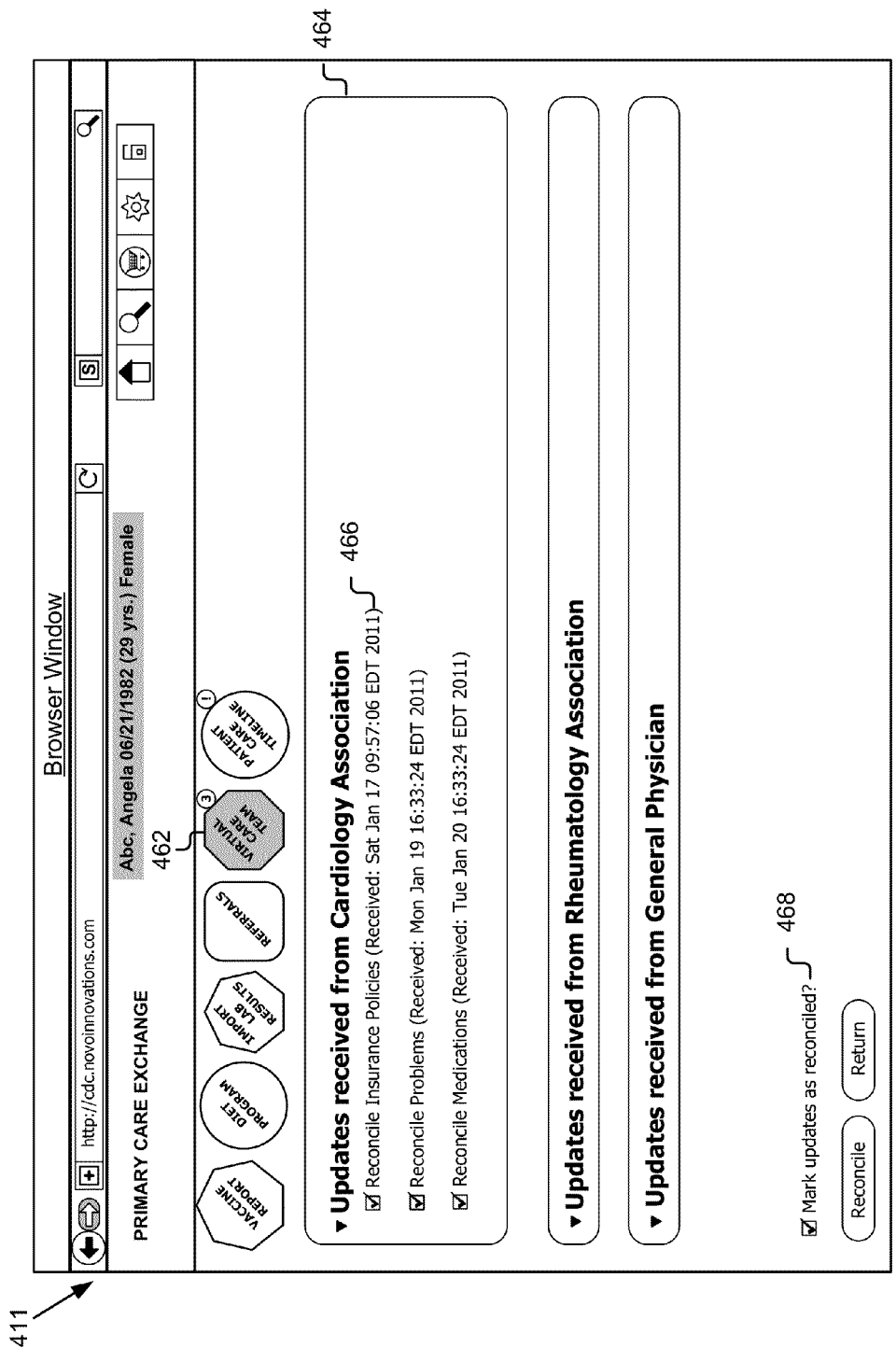
FIG. 4F is a graphical illustration of a user interface for viewing an application store according to one embodiment of the invention.

FIG. 4F is a graphic representation 411 of a user's view of reconciliatory updates procured by the virtual care team application 462 in order to reconcile patient records. The virtual care team application 462 displays an update tab 464 associated with different departments and/or institutions. In addition, the virtual care team application 462 displays a visible numeral indicating the number of updates to be reconciled. In this example, the virtual care team app 462 displays the number three. The update tab 464 associated with a department and/or institution comprises the day, the date, the time and the time zone for each individual update 466 received. In one embodiment, each update 466 needs to be authorized by the user to be reconciled by selecting the check box beside the update 466. In another embodiment, all the updates are reconciled at once without checking every individual update 466 by checking the reconcile icon underneath the "Mark updates as reconciled?" text 468.

Figure 4G:
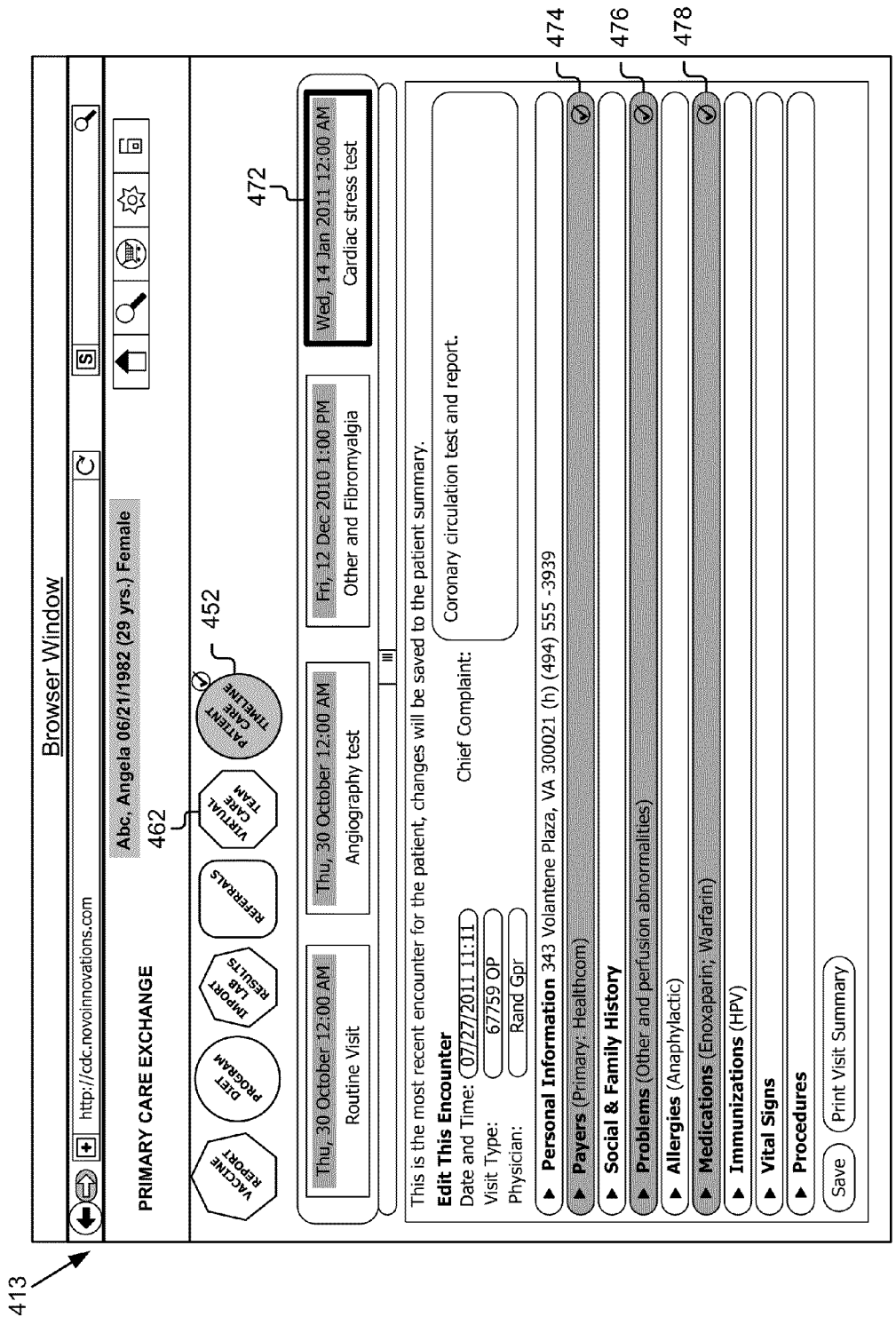
FIG. 4G is a graphical illustration of a user interface of a user's view of the timeline after reconciling a patient record with updates from another application according to one embodiment of the invention.

FIG. 4G is another graphic representation 413 of a user's view of the patient care timeline application 452 after reconciling a patient record with updates from the virtual care team application 462. The user interface engine 213 changes the patient care timeline application 452 appearance at least in part in response to the updates being reconciled in the virtual care team application 462 in FIG. 4F. In this embodiment, the patient care timeline application 452 displays the encounter that received the updates and the fields in the encounter that were updated by highlighting them to the user for at least a period of time. In this example, the cardiac stress test encounter 472 is highlighted and accompanying payers information tab 474, problems information tab 476 and medications information tab 478 after the user clicks on the patient care timeline 452.

Figure 4H:
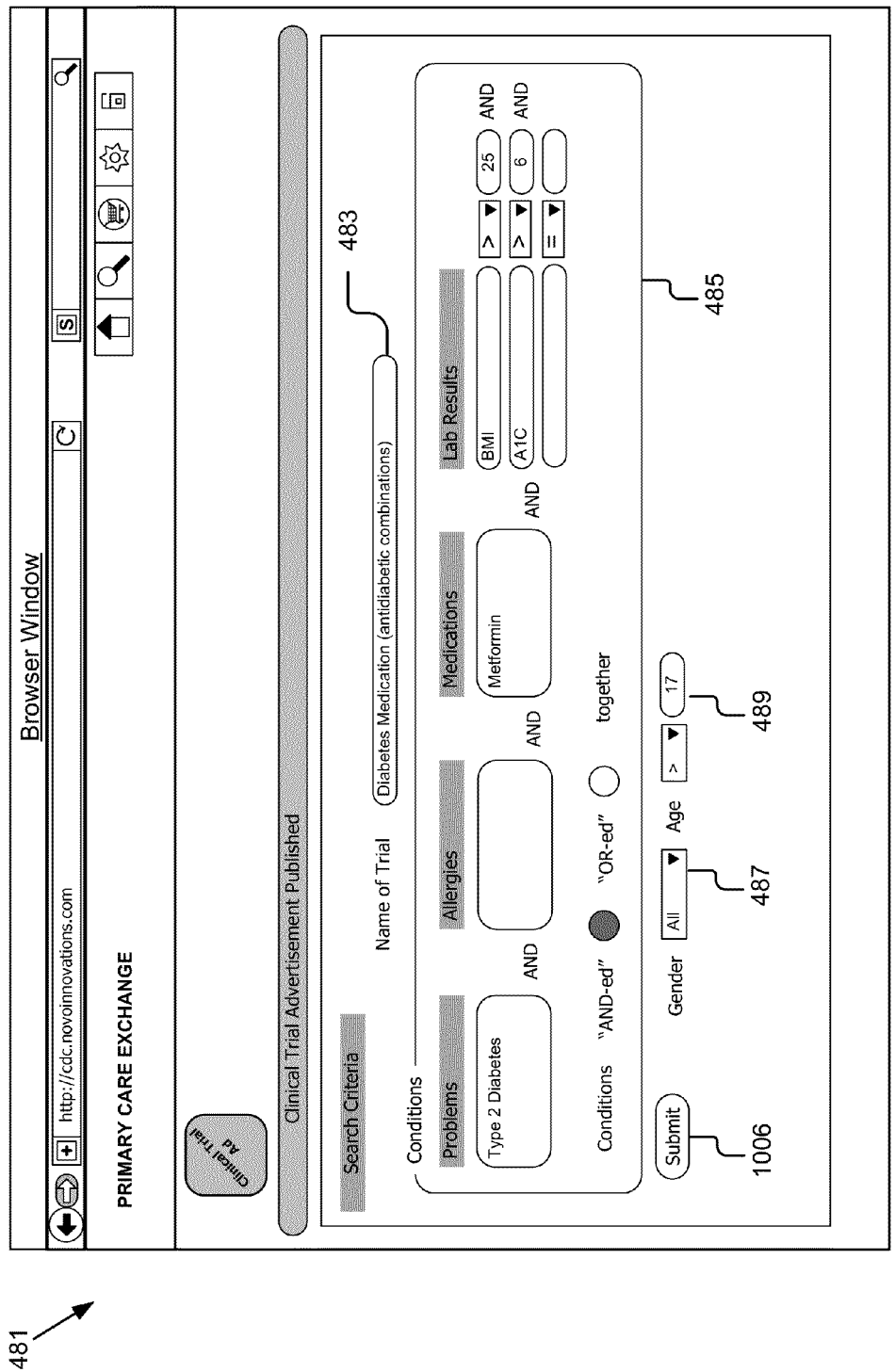
FIG. 4H is a graphical illustration of a user interface for requesting patient information.

Turning now to FIG. 4H, one embodiment of a user interface 481 generated by the user interface engine 213 for generating a request or advertisement for recruiting potential participants for a study is illustrated. The user interface 481 displays a plurality of inputs for generating a request. The plurality of inputs includes an input 483 for identifying or labeling the study. The user interface 481 displays input area 485 for capturing medical related criteria for creating input data that is used to identify patients for the study. In the example, input area 485 comprises diagnosis information, allergy information, medication information, and lab result information. User interface 481 displays a gender input 487 for identifying one or all genders for the study. User interface 481 displays an age input 489 for identifying an age or age group for the study. A user submits the request or advertisement by pressing the submit button 491. Persons of ordinary skill in the art will recognize that other variables can also be displayed for generating the request, such as a text box for specifying a location, previous illnesses, family history of illnesses, etc. The advertisement listing engine 372 receives the request and registers the request for identifying potential participants for the study.

Methods

Referring now to FIGS. 5-10, various example embodiments of the invention will be described.

Figure 5:
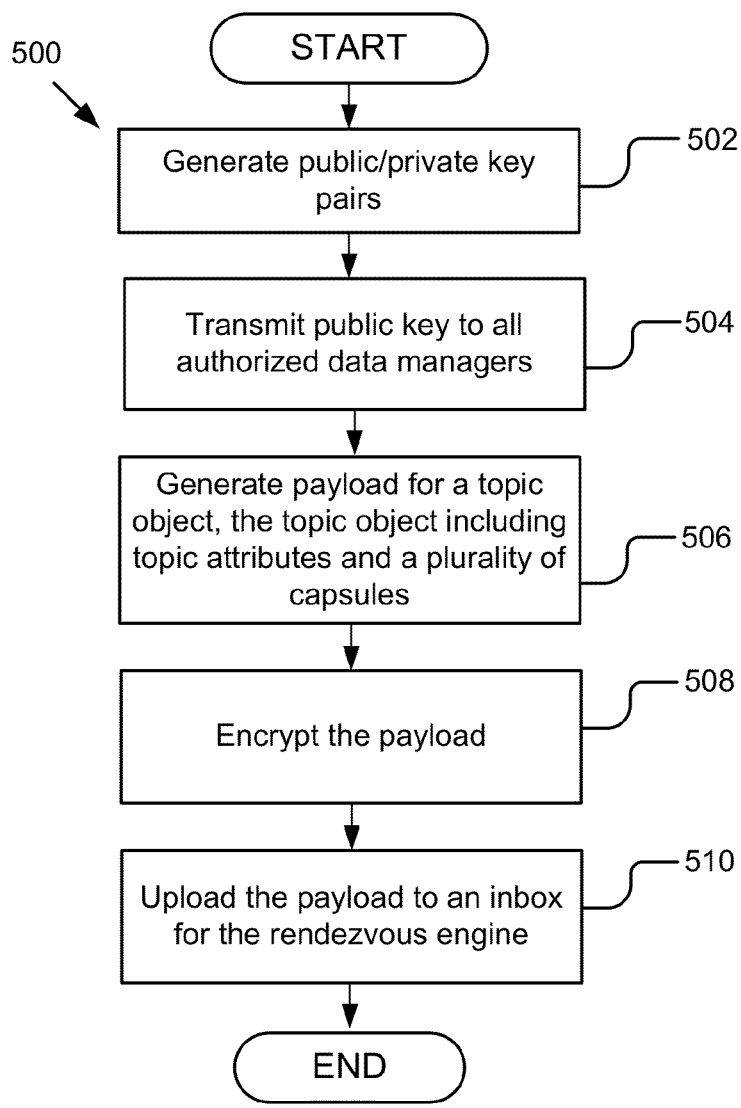
FIG. 5 illustrates a flowchart of a method for generating a payload according to one embodiment of the invention.

FIG. 5 is a flow diagram 500 illustrating one embodiment for generating a payload. A first data manager 103a includes a grid engine 203 that generates 502 public/private key pairs and transmits 504 the public key to all authorized data managers 103n. In one embodiment the public/private key pairs are generated with a 2048-bit RSA PKI. The grid engine 203 generates 506 a payload for a topic object, the topic object including topic attributes and a plurality of capsules. The grid engine 203 encrypts 508 the payload. In one embodiment, the grid engine 203 uses an AES symmetric key to encrypt the topic object. The grid engine 203 via the communication unit 245 uploads 510 the payload to an inbox for the rendezvous engine 200.

Figure 6:
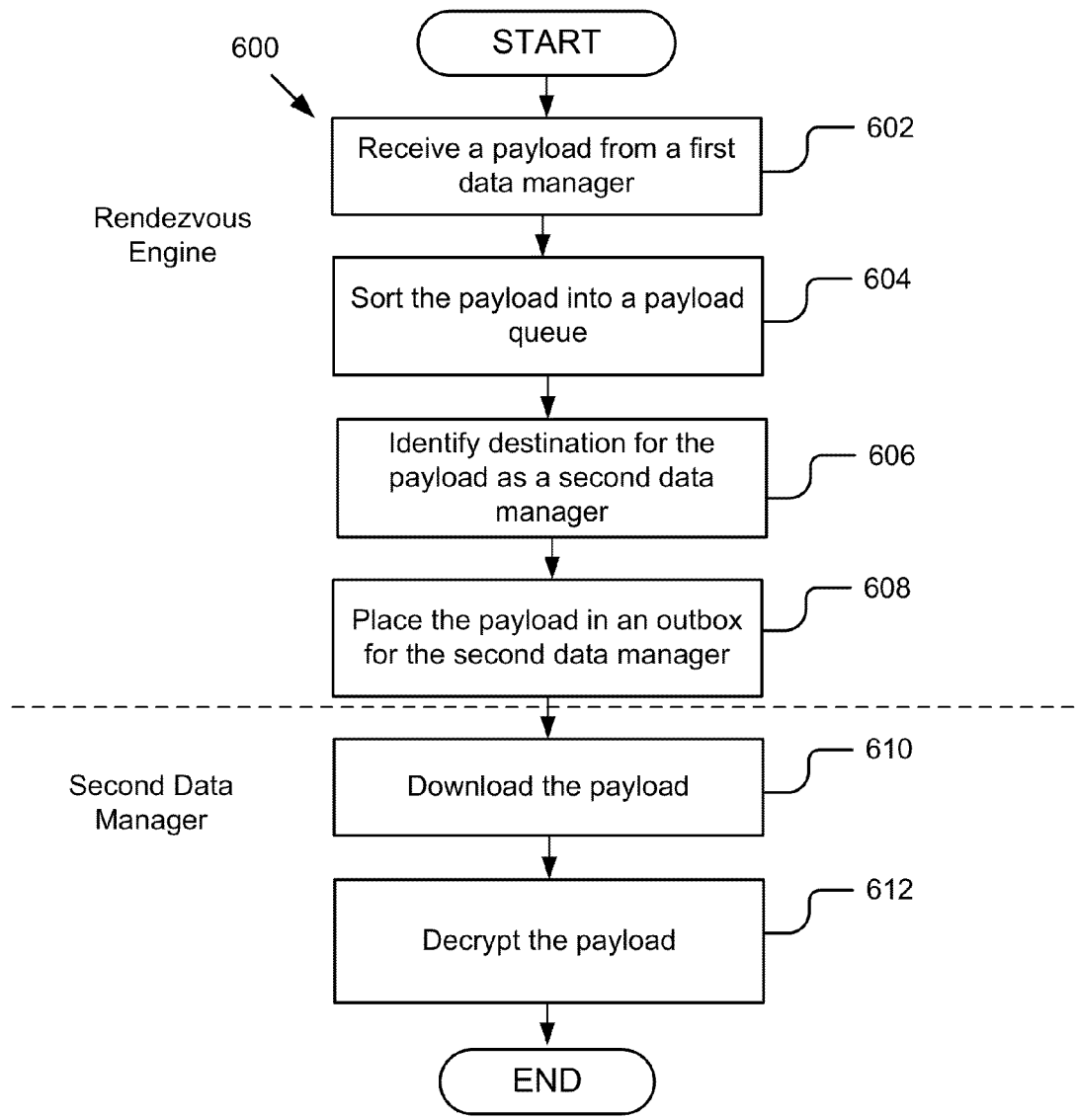
FIG. 6 illustrates a flowchart of a method for using a rendezvous engine to transmit data between data servers according to one embodiment of the invention.

FIG. 6 is a flow diagram 600 illustrating one embodiment for using a rendezvous engine 200 to transmit data between data managers 103n. The rendezvous engine 200 includes a sorter 206 that receives 602 a payload from a first data manager via the communication unit. The sorter 206 sorts 604 the payload into a payload queue 210. The sorter 206 identifies 606 the destination for the payload as a second data manager 103b. The sorter 206 places 608 the payload in an outbox for the second data manager 103b. The second data manager 103b downloads 610 the payload and decrypts 612 the payload.

Figure 7:
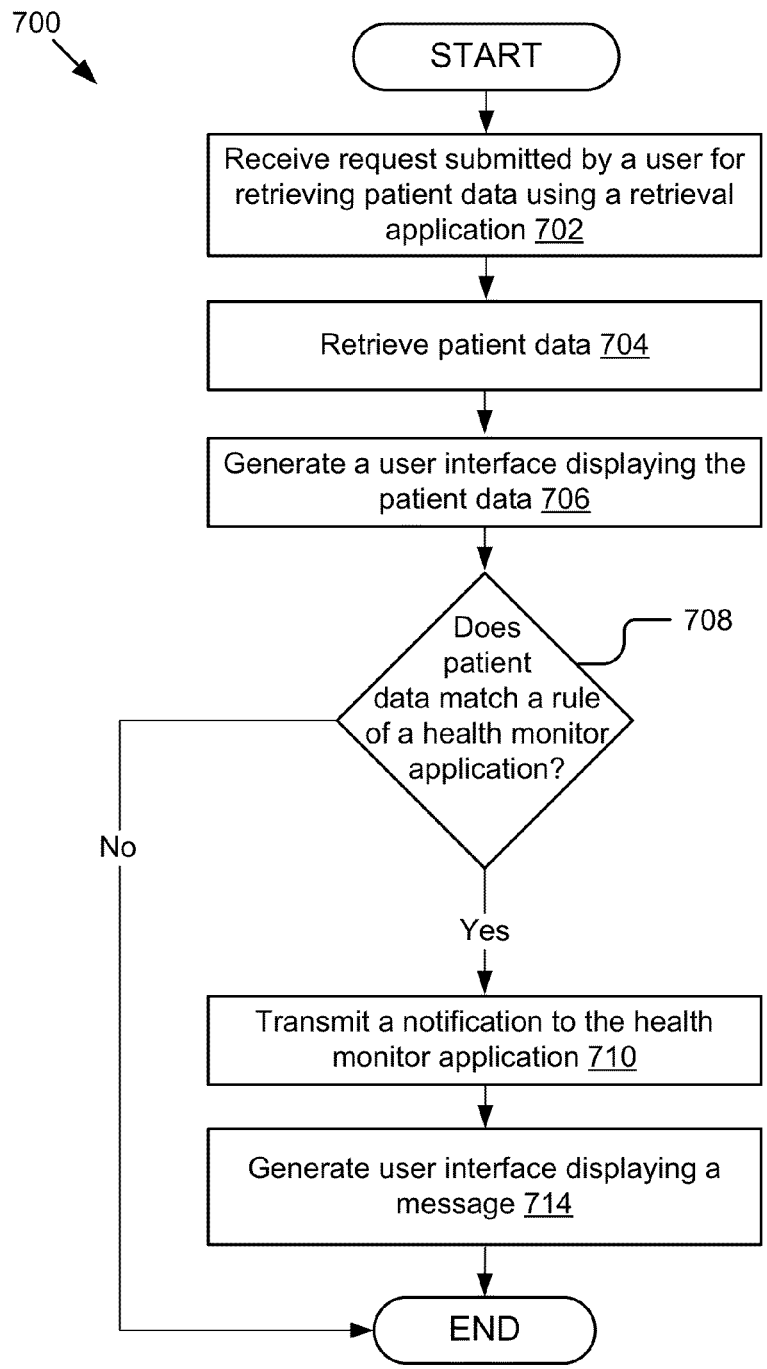
FIG. 7 illustrates a flowchart of a method for monitoring changes between applications according to one embodiment of the invention.

FIG. 7 is a flow diagram 700 illustrating one embodiment for transmitting a notification to an application based on a task performed by another application. The controller 201 receives 702 a request submitted by a user 125 for retrieving patient data using a retrieval application. The retrieval application retrieves 704 the patient data. For example, the retrieval application retrieves a virtual care team (VCT) record of a patient from the data storage 141. The user interface engine 213 generates 706 a user interface displaying the patient data. The application manager 207 includes a contextual module 308 that determines 708 whether the patient data matches a rule of a health monitor application. The contextual module 308 transmits 710 a notification to the health monitor application in response to determining that the patient data matches the rule. In this example, the contextual module 308 determines from the patient's VCT record that the patient's cholesterol level is higher than a threshold and transmits a notification to the health monitor application. The health monitor application instructs the user interface engine 213 to generate a user interface. The user interface engine 213 generates 714 a user interface displaying a message. In this example, the user interface displays a warning message that the patient's cholesterol level is too high.

Figure 8A:
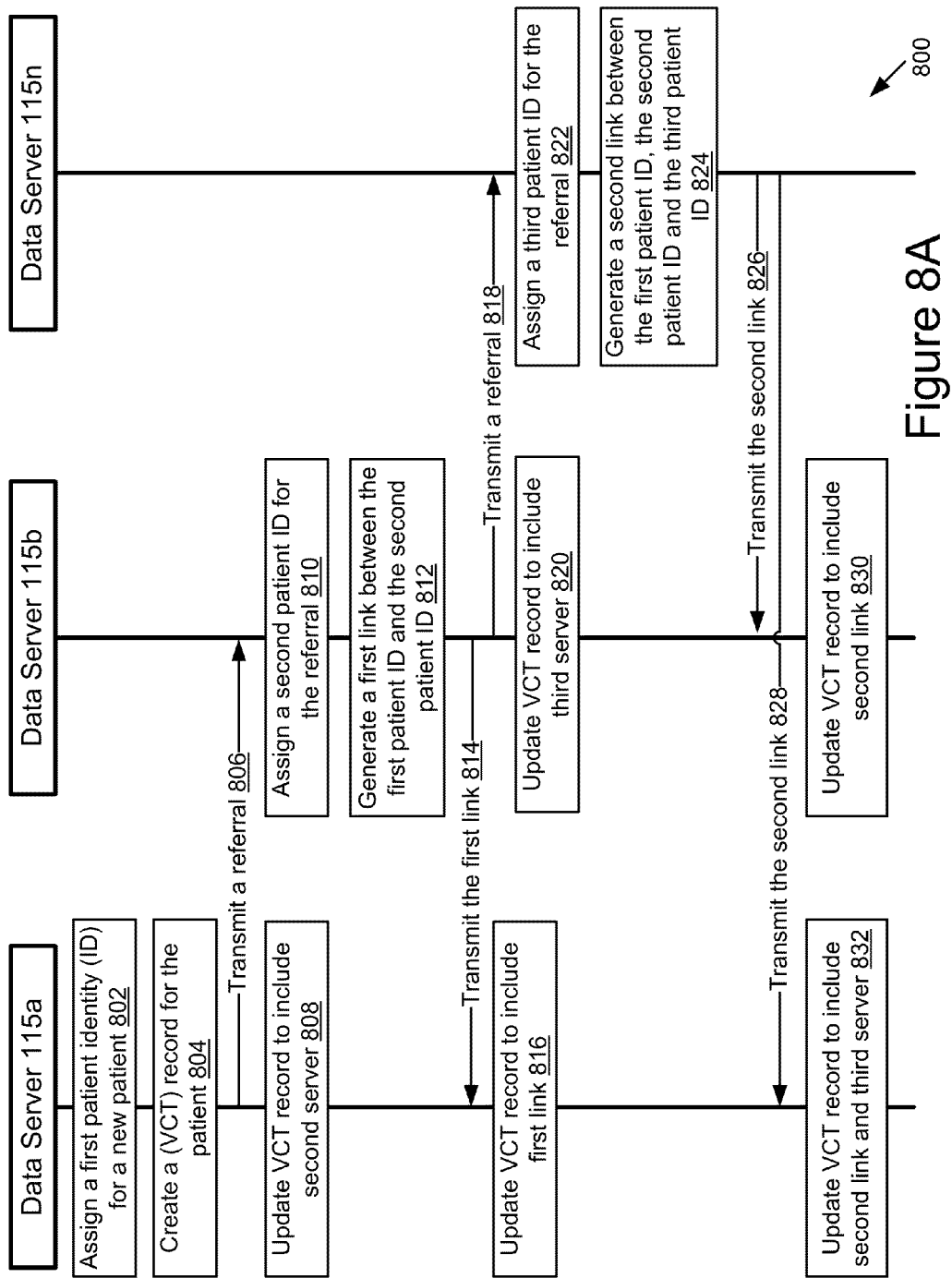
FIG. 8A illustrates a flowchart of a method for propagating patient identifiers between multiple data servers according to one embodiment of the invention.

FIG. 8A is a flow diagram 800 illustrating one embodiment for transmitting referrals. A VCT module 209 includes a creation module 352 that (for example, a primary care physician) assigns 802 a first patient identifier (ID) for a new patient. The creation module 352 creates 804 a VCT record for the patient. In this example, the primary care physician 115a diagnoses that the patient requires surgery on his knee and submits a request. The referral module 354 identifies a data server 115b (for example, an orthopedic surgeon) from the storage device 141. The controller 201 transmits 806 a referral to the data server 115b via the communication unit 245. The referral comprises a copy of the patient's VCT record that includes the first patient ID. The referral module 354 also updates 808 the VCT record to include the data server 115b as a member of the care team of the patient. The referral module 354 of the data server 115b assigns 810 a second patient ID for the referral based on the format requirements and the rules of the data server 115b. The referral module 354 generates 812 a first link between the first patient ID and the second patient ID. The controller 201 of the data server 115b then transmits 814 the first link to the data server 115a. The referral module 354 of the data server 115a updates 816 the VCT record to include the first link.

The referral module 354 of the data server 115b then identifies a data server 115n (for example, a physical therapist) for the patient. The controller 201 of the data server 115b transmits 818 a referral to the third data server 115*n*. This referral comprises a copy of the patient's VCT record that includes the second patient ID and the first link. The referral module 354 of the data server 115*b* updates 820 the VCT record to include the data server 115*n* as a member of the care team of the patient. The referral module 354 of the data server 115*n* assigns 822 a third patient ID for the referral. The referral module 354 of the data server 115*n* also generates 824 a second link between the first patient ID, the second patient ID and the third patient ID. The controller 201 of the data server 115*n* then transmits 826 the second link to the data server 115*b*. The referral module 354 of the second data server 115*b* updates 830 the patient's VCT record to include the second link. The controller 201 of the data server 115*n* also transmits 828 the second link to the data server 115*a*. The referral module 354 of the data server 115*a* updates 832 the patient's VCT record to include the second link and the data server 115*n* as a member of the patient's care team.

The links are advantageous in scenarios, for example, when the data server 115*a* receives health care information from the data server 115*b* that is represented by the second patient ID. In this example, the data server 115*a* easily identifies and retrieves the VCT record of the patient based on the first link. Furthermore, in this example, although the data server 115*n* was not referred by the data server 115*a*, the second link allows exchange of health care information associated with the patient between the data servers 115*a*, 115*b*, 115*n*.

Figure 8B:
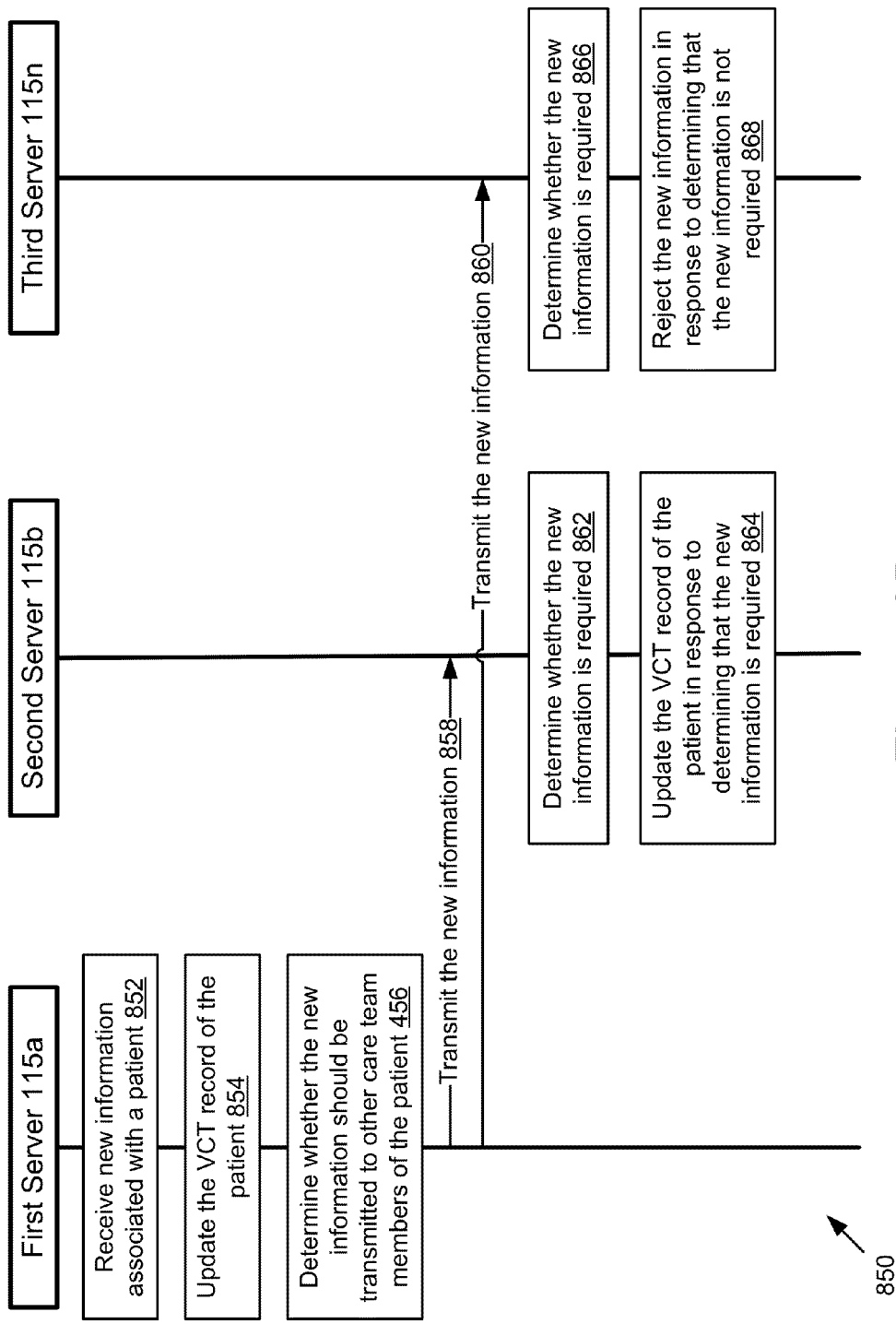
FIG. 8B illustrates a flowchart of a method for updating patient information between multiple data servers according to one embodiment of the invention.

FIG. 8B is a flow diagram 850 illustrating one embodiment for exchanging information between care team members of a patient. The data receiver 356 of the data server 115*a* receives 852 new information associated with a patient. The data receiver 356 updates 854 the VCT record of the patient with the new information. The data transmitter 358 of the data server 115*a* determines 856 whether the new information should be transmitted to other care team members of the patient. In response to determining that the new information should be transmitted, the data transmitter 358 transmits 858 the new information to the data server 115*b*. The data transmitter 358 also transmits 860 the new information to the data server 115*n*. The data receiver 356 of the data server 115*b* determines 862 whether the new information is required. The data receiver 356 updates 864 the VCT record of the patient in response to determining that the new information is required. The data receiver 356 of the data server 115*n* determines 866 whether the new information is required for the data server 115*n*. The data receiver 356 rejects 868 the new information in response to determining that the new information is not required for the data server 115*n*.

Figure 9:
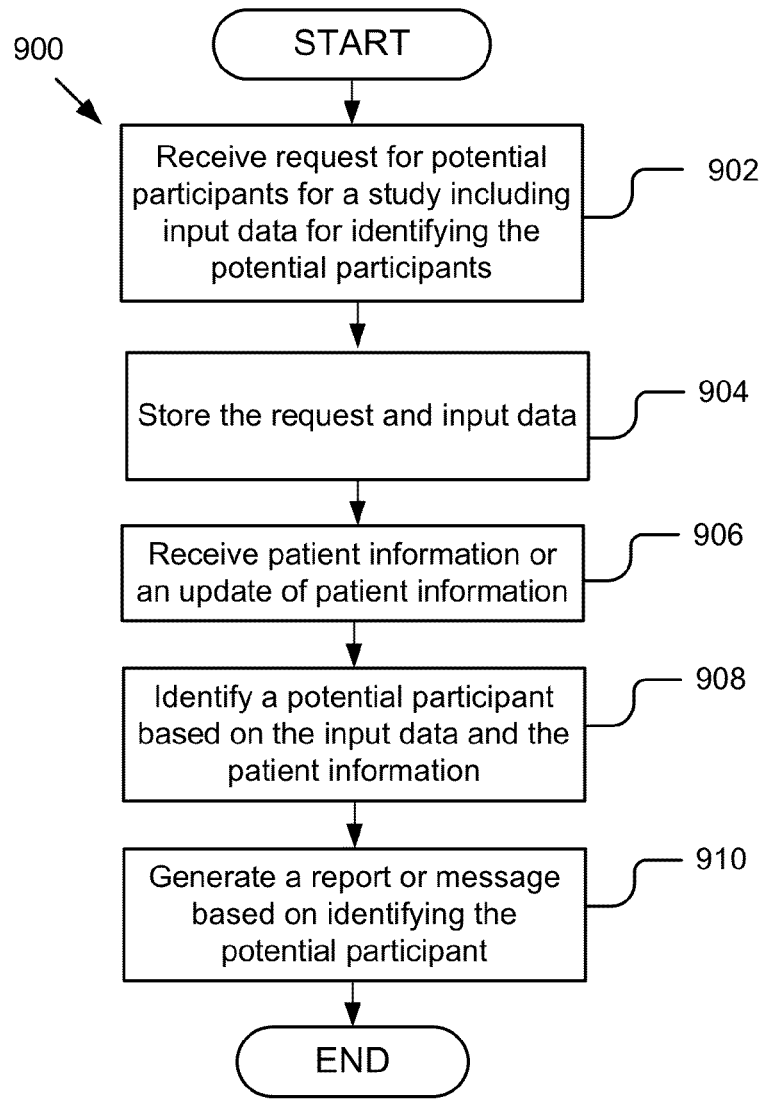
FIG. 9 illustrates a flowchart of a method for identifying participants of a study according to one embodiment of the invention.

FIG. 9 is a flow diagram 900 of one embodiment of a method for recruiting participants for a study. The advertisement listing engine 374 receives 902 a request for potential participants for a study including input data for identifying the potential participants. In one embodiment, the input data includes information relating to a diagnosis, medication, lab results, gender, age, location, etc. The advertisement listing engine 374 stores 906 the request and input data in the storage device 141. The participant identifying engine 372 receives 906 patient information or an update of patient information. The participant identifying engine 372 identifies 908 a potential participant based on the input data and the patient information. The advertisement response engine 378 generates 910 a report or message based on identifying the potential participant. In one embodiment, the advertisement engine 378 generates a message that an individual is a match for the study. In the embodiment, the message is sent to a provider of care or the individual. In another embodiment, the advertisement response engine 378 generates a message that includes statistics based on identifying one or more potential participants. In the embodiment, the advertisement response engine 378 sends the message to a clinical research organization that is recruiting participants for the study.

Figure 10:
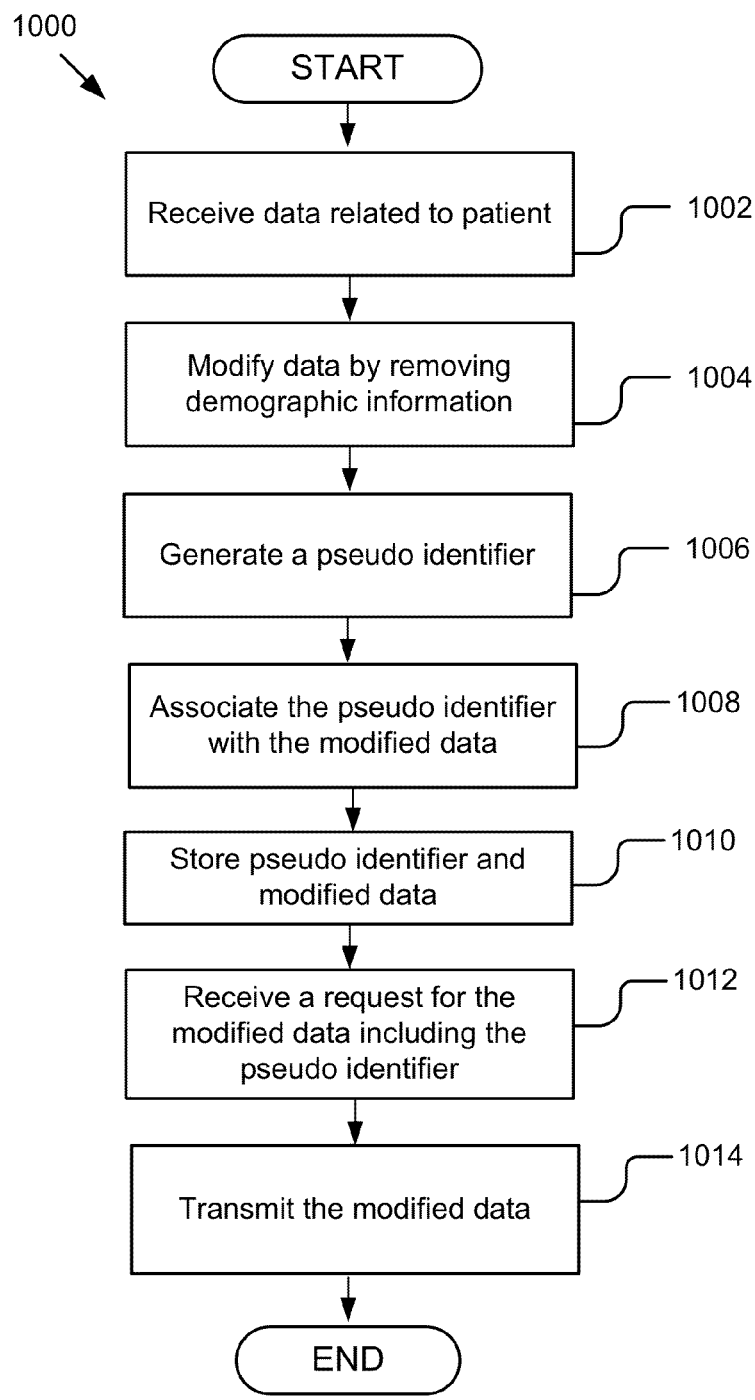
FIG. 10 illustrates a flowchart of a method for generating pseudo identifiers for patients according to one embodiment of the invention.

FIG. 10 is a flow diagram 1000 of one embodiment of a method for pseudoanonymising patient information. The data scrubbing engine 376 receives 1002 data related to a patient. In one embodiment, the data is related to an admission of a patient or a lab event. The data scrubbing engine 376 modifies 1004 the data by removing demographic information. In one embodiment, the data scrubbing engine 376 removes any key information for identifying an individual. For example, key information includes name, social security number or other government identifiers, birth date, mail address or race. In another embodiment, the data scrubbing engine 376 modifies the data by replacing demographic data that leads to identification of an individual. In one embodiment, the key information is determined by government standards for the purpose of protecting the identity of individuals. The pseudo identifier generator 378 generates 1006 a pseudo identifier for the modified data related to the patient. The data scrubbing engine 376 associates 1008 the pseudo identifier with the modified data related to the patient. The data scrubbing engine 376 stores 1010 the pseudo identifier and the modified data in the storage device 141. The data scrubbing engine 376 receives 1012 a request for the modified data including the pseudo identifier. The data scrubbing engine 376 retrieves the modified data based on the pseudo identifier and transmits 1014 the modified data to the requestor via the communication unit 245.

The foregoing description of the example embodiments of the invention has been presented for the purposes of illustration and description. It is not intended to be exhaustive or to limit the invention to the precise form disclosed. Many modifications and variations are possible in light of the above teaching. It is intended that the scope of the disclosure be limited not by this detailed description, but rather by the claims of this application. As will be understood by those familiar with the art, the invention may be embodied in other specific forms without departing from the spirit or essential characteristics thereof. Likewise, the particular naming and division of the modules, routines, features, attributes, methodologies and other aspects are not mandatory or significant, and the mechanisms that implement the invention or its features may have different names, divisions and/or formats. Furthermore, as will be apparent to one of ordinary skill in the relevant art, the modules, routines, features, attributes, methodologies and other aspects of the disclosure can be implemented as software, hardware, firmware or any combination of the three. Also, wherever a component, an example of which is a module, of the invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the disclosure is in no way limited to implementation in any specific programming language, or for any specific operating system or environment. Accordingly, the disclosure is intended to be illustrative, but not limiting, of the scope of the invention, which is set forth in the following claims.

What is claimed is:
1. A computer-implemented method for managing interactions between applications, the method comprising:

receiving, by one or more processors, a request to perform a first task using a first application;

performing, by the one or more processors, the first task using the first application;

modifying, by the one or more processors, a visual appearance of the first application responsive to the first task being performed;

analyzing, by the one or more processors, the request and a result of the first task performed by the first application;

determining, by the one or more processors, whether the analysis matches one or more rules associated with a second application;

transmitting, by the one or more processors, a notification to the second application; and modifying, by the one or more processors, a visual appearance of the second application based on the notification to indicate a request for reconciliation of the result between the first application and the second application.

2. The method of claim 1, further comprising performing a second task using the second application in response to determining that the analysis matches one or more rules associated with the second application.

3. The method of claim 2, further comprising generating a user interface in response to determining that the analysis matches one or more rules associated with the second application.

4. The method of claim 3, wherein the user interface displays at least one of a message indicating that the analysis matches one or more rules and a result of the second task.

5. The method of claim 3, wherein the user interface displays an icon indicating that information from the first application needs to be reconciled with the second application.

6. The method of claim 1, wherein the first application is developed by a user.

7. The method of claim 6, further comprising certifying the first application by determining whether the first application is compatible with the second application.

8. A system for managing interactions between applications comprising:

one or more processors;

a controller stored on a memory and executable by the one or more processors, the controller for receiving a request to perform a first task using a first application;

the first application stored on the memory and executable by the one or more processors, the first application coupled to the controller for performing the first task; and an application manager stored on the memory and executable by the one or more processors, the application manager coupled to the first application for modifying a visual appearance of the first application responsive to first task being performed, analyzing the request and a result of the first task performed by the first application, determining whether the analysis matches one or more rules associated with a second application, transmitting a notification to the second application and modifying a visual appearance of the second application based on the notification to indicate a request for reconciliation of the result between the first application and the second application.

9. The system of claim 8, further comprising the second application coupled to the application manager, the second application for performing a second task in response to determining that the analysis matches one or more rules associated with the second application.

10. The system of claim 9, further comprising a user interface engine coupled to the application manager, the user interface engine for generating a user interface in response to determining that the analysis matches one or more rules associated with the second application.

11. The system of claim 10, wherein the user interface engine displays an icon indicating that information from the first application needs to be reconciled with the second application.

12. The system of claim 8, wherein the first application is developed by a user.

13. The system of claim 8, wherein the application manager certifies the first application by determining whether the first application is compatible with the second application.

14. A computer program product comprising a computer useable medium including a computer readable program, wherein the computer readable program when executed on a computer causes the computer to:

receive a request to perform a first task using a first application;

perform the first task using the first application;

modify a visual appearance of the first application responsive to the first task being performed;

analyze the request and a result of the first task performed by the first application;

determine whether the analysis matches one or more rules associated with a second application;

transmit a notification to the second application; and modify a visual appearance of the second application based on the notification to indicate a request for reconciliation of the result between the first application and the second application.

15. The computer program product of claim 14, further comprising performing a second task using the second application in response to determining that the analysis matches one or more rules associated with the second application.

16. The computer program product of claim 15, further comprising generating a user interface in response to determining that the analysis matches one or more rules associated with the second application.

17. The computer program product of claim 16, wherein the user interface displays at least one of a message indicating that the analysis matches one or more rules and a result of the second task.

18. The computer program product of claim 16, wherein the user interface displays an icon indicating that information from the first application needs to be reconciled with the second application.

19. The computer program product of claim 14, wherein the first application is developed by a user.

20. The computer program product of claim 19, further comprising certifying the first application by determining whether the first application is compatible with the second application.

* * * * *